(12) United States Patent
Young

(10) Patent No.: US 7,501,234 B2
(45) Date of Patent: *Mar. 10, 2009

(54) STRESS PROTEINS AND USES THEREFOR

(75) Inventor: Richard A. Young, Weston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 277 days.

This patent is subject to a terminal disclaimer.

(21) Appl. No.: 11/401,608

(22) Filed: Apr. 10, 2006

(65) Prior Publication Data

US 2006/0177460 A1 Aug. 10, 2006

Related U.S. Application Data

(60) Continuation of application No. 10/880,771, filed on Jun. 28, 2004, now abandoned, which is a continuation of application No. 10/046,649, filed on Jan. 14, 2002, now abandoned, which is a division of application No. 08/336,251, filed on Nov. 3, 1994, now Pat. No. 6,338,952.

(51) Int. Cl.
*C12Q 1/00* (2006.01)
*A61K 39/00* (2006.01)

(52) U.S. Cl. .................. 435/4; 424/192.1; 424/277.1; 424/278.1

(58) Field of Classification Search ........................ None
See application file for complete search history.

(56) References Cited

U.S. PATENT DOCUMENTS

| | | | |
|---|---|---|---|
| 4,557,931 A | 12/1985 | Irie et al. | |
| 4,666,847 A | 5/1987 | Alford et al. | |
| 4,716,038 A | 12/1987 | Stanford et al. | |
| 4,724,144 A | 2/1988 | Rook et al. | |
| 4,734,362 A | 3/1988 | Hung et al. | |
| 4,784,941 A | 11/1988 | Watanabe et al. | |
| 4,797,359 A | 1/1989 | Finkelstein | |
| 4,918,164 A | 4/1990 | Hellstrom et al. | |
| 4,918,166 A | 4/1990 | Kingsmen et al. | |
| 5,114,844 A | 5/1992 | Cohen et al. | |
| 5,204,259 A | 4/1993 | Helting et al. | |
| 5,256,767 A | 10/1993 | Salk et al. | |
| 5,504,005 A | 4/1996 | Bloom et al. | |
| 5,580,563 A | 12/1996 | Tam | |
| 5,925,362 A | 7/1999 | Spitler et al. | |
| 6,030,618 A | 2/2000 | Srivastava | |
| 6,335,183 B1 | 1/2002 | Young | |
| 6,338,952 B1 | 1/2002 | Young | |
| 6,403,099 B1 | 6/2002 | Rappuoli et al. | |
| 6,455,493 B1 | 9/2002 | Wallen et al. | |
| 6,482,614 B1 | 11/2002 | Young | |
| 6,495,347 B1 | 12/2002 | Siegel et al. | |
| 6,875,435 B2 | 4/2005 | Huang et al. | |
| 2001/0005713 A1 | 6/2001 | Young | |
| 2002/0146426 A1 | 10/2002 | Huang et al. | |
| 2003/0073094 A1 | 4/2003 | Young et al. | |
| 2004/0204363 A1 | 10/2004 | Young | |
| 2005/0048079 A1 | 3/2005 | Huang et al. | |
| 2005/0163792 A1 | 7/2005 | Young et al. | |
| 2006/0177461 A1 | 8/2006 | Young et al. | |

FOREIGN PATENT DOCUMENTS

| | | |
|---|---|---|
| EP | 0 118 393 A2 | 9/1984 |
| EP | 0 230 222 A1 | 7/1987 |
| EP | 0 262 710 | 9/1987 |
| EP | 0 322 990 | 7/1989 |
| EP | 0 521 220 A1 | 1/1993 |
| GB | 2 251 186 | 7/1992 |
| JP | 1-179687 | 7/1989 |
| JP | 01-179687 | 7/1989 |
| JP | 2-501107 | 4/1990 |
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO 90/12030 | 9/1990 |
| WO | WO 91/15572 | 10/1991 |
| WO | WO 92/08484 | 5/1992 |
| WO | WO 92/08488 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 96/10421 | 4/1996 |
| WO | WO 97/06821 | 2/1997 |
| WO | WO 97/26910 | 7/1997 |
| WO | WO 98/23735 | 6/1998 |
| WO | WO 98/35705 | 8/1998 |
| WO | WO 99/07860 | 2/1999 |
| WO | WO 01/51081 | 7/2001 |
| WO | WO 90/15873 | 12/1990 |
| WO | WO 91/02542 | 3/1991 |

OTHER PUBLICATIONS van der Bruggen et al., Science, 1991, 254(5038):1643-1647.*
Stover, C.K., et al., *Nature*, vol. 351, (Jun. 6, 1991), pp. 456-460.
Agranovsky, A.A., et al., "Putative 65 kDa Protein of Beet Yellows Closterovirus is a Homologue of HSP70 Heat Shock Proteins," *J. Mol. Biol.*, 217:603-610 (1991).

(Continued)

*Primary Examiner*—Stacy B Chen
(74) *Attorney, Agent, or Firm*—Hamilton, Brook, Smith and Reynolds, P.C.

(57) ABSTRACT

The present invention relates to stress proteins and methods of modulating an individual's immune response. In particular, it relates to the use of such stress proteins in immune therapy and prophylaxis, which results in an induction or enhancement of an individual's immune response and as an immunotherapeutic agent which results in a decrease of an individual's immune response to his or her own cells. The present invention also relates to compositions comprising a stress protein joined to another component, such as a fusion protein in which a stress protein is fused to an antigen. Further, the present invention relates to a method of generating antibodies to a substance using a conjugate comprised of a stress protein joined to the substance.

10 Claims, 10 Drawing Sheets

OTHER PUBLICATIONS

Agterberg, M., et al., "Outer Membrane Protein PhoE as a Carrier for the Exposure of Foreign Antigenic Determinants at the Bacterial Cell Surface," *Antonie Van Leeuwenhoek* 59:249-262 (1991).

Agterberg, M., et al., "Outer Membrane PhoE Protein of *Escherichia coli* as a Carrier for Foreign Antigenic Determinants: Immunogenicity of Epitopes of Foot-and-Mouth Disease Virus," *Vaccine* 8:85-91 (Feb. 1990).

Agterberg, M., et al., "Protection of Guinea-pigs Against Foot-and-Mouth Disease Virus by Immunization with a PhoeE FMDV Hybrid Protein," *Vaccine* 8:438-440 (Oct. 1990).

Aldovini, et al., "Humoral and Cell-Mediated Immune Responses to Live Recombinant BCG-HIV Vaccines," *Nature* 351(6326):479-482 (Jun. 1991).

Allen, P.M., et al., "T-Cell Recognition of Lysozyme: The Biochemical Basis of Presentation," *Immunol. Rev.* 98:171-187 (1987).

Amadori, M. et al., "Chaperonin 10 0 fMycobacteroum tuberculosis Induces a Protective Immune Response to Foot-and-Mouth Disease Virus," *Arch Virol.* 144:905-919 (1999).

Amory Siosson, L.M., et al., "Induction of Protective Immunity in Mice Using A 62-kDa Recombinant Fragment of a *Schistosoma mansoni* Surface Antigen," *J. of Immunol.*, 149(11):3612-3620 (1992).

Anthony, L.S.D., et al., "Induction of HbcAg-Specific CTL Responses by a Heat Shock Protein Fused to the Core Antigen of the Hepatitis B Virus," Abstract S16 in the Final Program and Abstracts Book for The Fifth Annual Conference on Vaccine Research, held May 6-8, 2002.

Anthony, L.S.D., et al., "Priming of CD8+ CTL Effector Cells In Mice By Immunization With A Stress Protein-Influenza Virus Nucleoprotein Fusion Molecule," *Vaccine* 17:373-383 (1999).

Ardeshir, et al., "A 75 Kd Merozoite Surface Protein of Plasmodium Falciparum which is Related to the 70 kd Heat-Shock Proteins," *EMBO J.*, 6(2):493-499 (1987).

Arnosti, et al., "Characterization of Heat Shock," *J. Bacterol.* 168(3):1243-1249 (Dec. 1986).

Arrigo, A. and Welch, W.J., "Characterization and Purification of the Small 28,000-Dalton Mammalian Heat Shock Protein," *J. Biol. Chem.*, 262(32):15359-15369 (1987).

Babbitt, et al., "Binding of Immunogenic Peptides to Ia Histocompatibility Molecules," *Nature* 317:359-361 (1985).

Ballard, et al., "Anthrax Toxin-Mediated Delivery in Vivo and In Vitro of a Cytotoxic T-Lymphocyte Epitope from Ovalbumin," *Infect. Immunol.* 66(2):615-619 (1998).

Bardwell, et al., "The Nucleotide Sequence of the *Escherichia coli* K12 dnaJ+ Gene," *J. Biol. Chem.*, 261(4):1782-1785 (Feb. 1986).

Barouch, et al., "Eventual AIDS Vaccine Failure in a Rhesus Monkey By Viral Escape From Cytotoxic Lymphocytes," *Nature* 415:335-339 (2002).

Barrios, C., et al., "Mycobacterial heat-shock proteins as carrier Molecules. II: The use of the 70-kDa mycobacterial heat-shock protein as carrier for conjugated vaccines can circumvent the need for adjuvants and Bacillus Calmette Guerin priming," *Eur. J. Immunol.*, 22:1365-1372 (1992).

Barrios, C. et al., "Heat shock proteins as carrier molecules: in vivo helper effect mediated by *Escherichia coli* GroEl and DnaK proteins requires cross-linking with antigen," *Clin. Exp. Immunol.*, 98:229-233 (1994).

Bayliss, C.D., et al., "A Recombinant Fowlpox Virus That Expresses the VP2 Antigen of Infectious Bursal Disease Virus Induces Protection Against Mortality Caused by the Virus," *Arch Virol.* 120:193-205 (1991).

Belz, et al., "A Previously Unrecgonized H-2Db-Restricted Peptide Prominent in the Primary Influenza a Virus-Specific CD8+ T-Cell Response Is Much Less Apparent Following Secondary Challenge," *J. Virol.* 74(8):3486-3493 (2000).

Bennett, S.R.M., et al., "Help for Cytotoxic-T-cell Responses is Mediated by CD40 Signalling," *Nature* 393:478-480 (Jun. 4, 1998).

Bertelli, M.S., et al., "BCG-Induced Resistance in *Trypanosoma cruzi* Experimental Infections," *Trop. Med. Parasitol*, 32:93-96 (1981).

Billman-Jacobe, H., et al., "Mapping of the T and B Cell Epitopes of the *Mycobacterium bovis* Protein, MPB70," *Immunol. Cell Biol.* 68:359-365 (1990).

Blachere, N.E. et al., "Heat Shock Protein-Peptide Complexes, Reconstituted In Vitro, Elicit Peptide-specific Cytotoxic T Lymphocyte Response and Tumor Immunity," *J. Exp. Med.* 186(8):1315-1322 (Oct. 20, 1997).

Blachere, N.E., et al., "Heat Shock Protein Vaccines Against Cancer," *J. Immunotherapy* 14(4):352-356 (1993).

Blander, S.J. and Horwitz, M.A., "Major Cytoplasmic Membrane Protein of *Legionella pneumophila*, a Genus Common Antigen and Member of the hsp 60 Family of Heat Shock Proteins, Induces Protective Immunity in a Guinea Pig Model of Legionnaires' Disease," *J. Clin. Invest.*, 91:717-723 (1993).

Bowie, et al., "Deciphering the Message in Protein Sequences: Tolerance to Amino Acid Substitutions," *Science* 247(4948):1306-1310 (1990).

Breloer, M., et al., "In Vivo and In Vitro Activation of T Cells After Administration of Ag-Negative Heat Shock Proteins," *J. of Immun.* 162:3141-3147 (1999).

Brett, et al., "Differential Pattern of T Cell Recognition of the 65-kDA Mycobacterial Antigen Following Immunization with the Whole Protein or Peptides," *Euro. J. Immunol.* 19:1303-1310 (1989).

Brett, S.J., et al., "Influences of Antigen Processing on the Expression of the T Cell Repertoire," *J. Exp. Med.* 168:357373 (Jul. 1988).

Brewer, S.J., et al., "Engineering Proteins to Enable Their Isolation in a Biologically Active Form," *Purification and Analysis of Recombinant Proteins*, Seltharam and Sharma, eds. (NY: Marcel Dekker, Inc.) (1991).

Britton, et al., "The Characterization and Immunoreactivity of a 70 KD Protein Common to *Mycobacterium leprae* and *Mycobacterium bovis* (BCG)," *Lepr. Rev., 57 Supp.* 2:67-75 (1986).

Burrows, P.D., et al., "B-Cell Development in Man," *Curr. Opin. Immunol.* 5:201-206 (1993).

Butini, et al., "Comparative Analysis of . . . ," *J. Cell. Biochem., Suppl. 18B*, Abstract J306 (1994).

Cane, P.A., et al., "Reduction of Yellow Fever Virus Mouse Neurovirulence by Immunization with a Bacterially Synthesized Non-structural Protein (NS1) Fragment," *J. Gen. Virol.* 69:1241-1246 (1988).

Cassell, W.A., et al., "Viral Oncolysate in the Management of Malignant Melanoma, I. Preparation of the Oncolysate and Measurement of Immunologic Responses" *Cancer*, 40:672-679 (Aug. 1977).

Cassell, W.A., et al., "A Phase II Study on the Postsurgical Management of Stage Malignant Melanoma With a Newcastle Disease Virus Oncolysate," *Cancer*, 52:856-860 (Sep. 1983).

Catelli, M.G., et al., "The common 90-kd protein component of non-transformed '8S' steroid receptors is a heat-shock protein," *EMBO J.*, 4(12):3131-3135 (1985).

Chandrasekhar, G.N., et al., "Purification and Properties of the groES Morphogenetic Protein of *Escherichia coli*," *J. Biol. Chem.* 261(26):12414-12419 (1986).

Chen, W., et al., "Human 60-kDa Heat-Shock Protein: A Danger Signal to the Innate Immune System," *J. Immunol.* 162:3212-3219 (1999).

Chong, P., et al., "Identification of a Potent Synthetic HIV1 Immunogen Comprising gag-P24 Tandem T-and B-Cell Epitopes," *FEBS Lett.* 264(2):231-234 (May 1990).

Chu, N.R., et al., "Immunotherapy of a Human Papillomavirus (HPV) Type 16 E7-Expressing Tumour by Administration of Fusion Protein Comprising *Mycobacterium bovis* Bacille Calmette-Guérin (BCG) hsp65 and HPV16 E7," *Clin. Exp. Immunol.* 121:216-225 (2000).

Ciborowski, P., et al., "Immunological response to a *Staphylococcus aureus* fibronectin-binding protein," *J. Med. Microbiol*, 37:376-381 (1992).

Ciupitu, A.T., et al., "Immunization with a Lymphocytic Choriomeningitis Virus Peptide Mixed with Heat Shock Protein 70 Results in Protective Antiviral Immunity and Specific Cytotoxic T Lymphocytes," *J. Exp. Med.* 187(5):685-691 (Mar. 2, 1998).

Clarke, B.E., et al., "Presentation and immunogenicity of viral epitopes on the surface of hybrid hepatitis B virus core particles produced in bacteria," *J. Gen. Virol.*, 71:1109-1117 (1990).

Clarke, B.E., et al., "Improved Immunogenicity of a Peptide Epitope After Fusion to Hepatitis B Core Protein," *Nature* 330:381-384 (Nov. 1987).

Clough, E.R., et al., "Production of Anti-Sporozoite Antibodies in Absence of Response to Carrier By Coupling an MDP Derivative to a Malaria Peptide-Tetanus Toxoid Conjugate," *Biochem. Biophys. Res. Commun.*, 131(1):70-75 (1985).

Cohen, J., "Jitters Jeopardize AIDS Vaccine Trials," *Science* 262:980-981 (1993).

Cox, et al., "Orientation of Epitopes Influences the Immunogenicity of Synthetic Peptide Dimers," *Euro. J. Immunol.* 18:2015-2019 (1988).

Crane, M.S., et al., "Cross-Protection Against Four Species of Chicken Coccidia with a Single Recombinant Antigen," *Infect. Immunol.* 59(4):1271-1277 (Apr. 1991).

Davis, et al., "Immune Response to Human Influenza Virus Hemagglutinin Expressed in *Escherichia coli*," *Gene*, 21(3):273-284 (Mar. 1983).

De Valesco, E.A., et al., "Synthetic Peptides Representing T-Cell Epitopes Act as Carriers in Pneumococcal Polysacchraride Conjugate Vaccines," *Infect. Immunol.*, 63(3):961-968 (1995).

Del Giudice, et al., "Heat Shock Proteins as "Super"—Carriers for Sporozite Vaccines?," *Res. Immunol.*, 142(8):703-707 (1991).

Del Giudice, G.D., et al., "Priming to Heat Shock Proteins in Infants Vaccinated against Pertussis," *J. Immunol.*, 150(5):2025-2032 (1993).

Delmas, A., et al., "Studies of the Influence of Different Cross-Linking Reagents on the Immune Response against a B-Epitope," *Bioconjug. Chem.* 3(1):80-84 (1992).

DeNagel, D.C. and Pierce, S.K., "Heat Shock Proteins in Immune Responses," *Crit. Rev. Immunol.*, 13(1):71-81 (1993).

Derkay, C.S.I., et al., "Hsp E7 Treatment of Pediatric Recurrent Respiratory Papillomatosis (RRP): Final Results of an Open-Label Trial," Abstract 633 on p. 443 of the Final Program for the 21st International Papilomavirus Conference & Clinical Workshop (2004).

Dintzis, R.Z., "Rational Design of Conjugate Vaccines," *Pediatr. Res.* 32(4):376-385 (1992).

Drew, M.D., et al., "Vaccination By Cholera Toxin Conjugated to a Herpes Simplex Virus Type 2 Glycoprotein D Peptide," *J. Gen. Virol.* 73:2357-2366 (1992).

DuBois, G.C., et al., "Isolation of a Tumor-Associated Transplantation Antigen (TATA) From an SV40-Induced Sarcoma. Resemblance to the TATA of Chemically Induced Neoplasms," *Int. J. Cancer*, 34:561-566 (1984).

Einstein, M.H., et al., Heat Shock Protein (HSP)-Based Immunotherapy (HspE7) for Treatment of CIN III (NCI 5850, NYGOG), Abstract 8 in the Abstract Book and Final Program for The Annual Meeting on Women's Cancer™; The Society of Gynecologic Oncologists' 36th Annual Meeting, Mar. 19-23, 2005.

Elias, D., et al, "Induction and therapy of autoimmune diabetes in the non-obese diabetic (NOD/Lt) mouse by a 65-kDa heat shock protein," *Proc. Natl. Acad. Sci. USA*, 87:1576-1580 (1990).

Emmrich, F., et al., "A Recombinant 64 Kilodalton Protein of *Mycobacterium bovis* Bacillus Calmette-Guerin Specifically Stimulates Human T4 Clones Reactive to Mycobacterial Antigens," *J. Exp. Med.* 163:1024-1029 (Apr. 19863).

Engel, et al., "Generation of Antibodies Against Human hsp and Murine hsp25 by Immunization with a Chimeric Small Heat Shock Protein," *Biomed. Biochim. Acta* 50:1065-1071 (1991).

Etlinger, H.M., et al., "Antibody Responses to a Synthetic Peptide-Based Malaria Vaccine Candidate: Influence of Sequence Variants of the Peptide," *Eur. J. Immunol.* 21:1505-1511 (1991).

Falk, R.E., et al., "Cell Mediated Immunity to Human Tumors," *Arch. Surg.*, 107:261-265 (Aug. 1973).

Farrelly, et al., "Complete Sequence of the Heat Shock-Inducible HSP90 Gene of *Saccharomyces cerevisiae*," *J. Biol. Chem.*, 259(9):5745-5751 (May 1984).

Ferrero, R.L. et al., "The GroES homolog of *Helicobacter pylori* confers protective immunity against mucosal infection in mice," *Proc. Natl. Acad. Sci. USA*, 92:6499-6503 (1995).

Finnegan, A., et al., "The T Cell Repertoire For Recognition of a Phylogenetically Distant Protein Antigen—Peptide Specificity and MHC Restriction of Staphylococcal Nuclease-specific T Cell Clones," *J. Exp. Med.* 164:897-910 (Sep. 1986).

Flaherty, K., et al., "Three-dimensional Structure of the ATPase Fragment of a 70K Heat-Shock Cognate Protein," *Nature* 346:623-628 (Aug. 16, 1990).

Francis, et al., "Peptide Vaccines Based on Enhanced Immunogenicity of Peptide Epitopes Presented with T-Cell Determinants or Hepatitis B Core Protein," *Methods Enzymol.* 178:659-676 (1989).

Francis, M.J., et al., "Non-Responsiveness to a Foot-and-Mouth Disease Virus Peptide Overcome by Addition of Foreign Helper T-Cell Determinants," *Nature* 330:168-170 (Nov. 1987).

Freimuth, P., et al., "Insertion of Myoglobin T-Cell Epitopes Into the *Escherichia coli* Alkaline Phosphatase," *Res. Microbiol.* 141:995-1001 (1990).

Friedland, J.S. et al., "Mycobacterial 65-kD heat shock protein induces release of proinflammatory cytokines from human monocytic cells," *Clin. Exp. Immunol.*, 91:58-62 (1993).

Fuqua, S.A.W., et al., "Induction of the Estrogen-regulated "24K" Protein by Heat Shock," *Cancer Res.* 49:4126-4129 (Aug. 1, 1989).

Fyfe, et al., "Murine Immune Response to HIV-1 p24 Core Protein Following Subcutaneous, Intraperitoneal and Intravenous Immunization," *Immunology* 74:467-472 (1991).

Gammon, G., et al., "The Choice of T-Cell Epitopes Utilized on a Protein Antigen Depends on Multiple Factors Distant from, as well as at the Determinant Site," *Immunol. Rev.* 98:53-73 (1987).

Gariepy, J., et al., "Vectorial Delivery of Macromolecules Into Cells Using Peptide-Based Vehicles," *Trends Biotechnol.* 19(1):21-28 (2001).

Garsia, et al., "Homology of the 70-Kilodalton Antigens from *Mycobacterium leprae* and *Mycobacterium bovis* with the Mycobacterium tuberculosis 71-Kilodalton Antigen and with the Conserved Heat Shock Protein 70 of Eucaryotes," *Infect. Immun.*, 57(1):204-212 (Jan. 1989).

Gelber, R.H., et al., "Vaccination With Pure *Mycobacterium leprae* Proteins Inhibits *M. leprae* Multiplication in Mouse Footpads," *Infect. Immun.* 62(10):4250-4255 (Oct. 1994).

Geluk, A., et al., "Functional Analysis of DR17(DR3)-Restricted Mycobacterial T Cell Epitopes Reveals DR17-Binding Motif and Enables The Design of Allele-Specific Competitor Peptides," *J. Immunol.* 149(9):2864-2871 (Nov. 1, 1992).

Goldstone, S.E., et al., "Activity of HspE7, a Novel Immunotherapy, in Patients with Anogenital Warts," *Dis. Colon Rectum* 45:502-507 (2002).

Gomes, et al., "Heat Shock Protein Synthesis During Development . . .," *J. Bacteriol.* 168(3):923-930 (Nov. 1986).

Gomez, F.J., et al., "Vaccination with Recombinant Heat Shock Protein 60 from *Histoplasma capsulatum* Protects Mice against Pulmonary Histoplasmosis," *Infect. Immun.*, 63:2587-2595 (1995).

Gomez, et al., "An 80-Kilodalton Antigen from *Histoplasma capsulatum* That Has Homology to Heat Shock Protein 70 Induces Cell-Mediated Immune Responses and Protection in Mice," *Infect. Immun.*, 60(7):2565-2571 (Jul. 1992).

Good, M.F., et al., "Construction of Synthetic Immunogen: Use of New T-Helper Epitope on Malaria Circumsporozoite Protein," *Science* 235:1059-1062 (Feb. 1987).

Grange, J.M., et al., "Tuberculosis and Cancer: Parallels in Host Responses and Therapeutic Approaches?," *The Lancet* 345:1350-1352 (1995).

Gupta, R.K., et al., "Adjuvants—a Balance Between Toxicity and Adjuvanticity," *Vaccine* 11:293-306 (2002).

Haghbin, M., et al., "Immunotherapy with Oral BCG and Serial Immune Evaluation in Childhood Lymphoblastic Leukemia Following Three Years of Chemotherapy," *Cancer*, 46:2577-2586 (Dec. 1980).

Handman, E., et al., "Leishmania major: Production of Recombinant gp63, Its Antigenicity and Immunogenicity in Mice," *Exp. Parasitol.* 70:427-435 (1990).

Hawiger, J., "Noninvasive Intracellular Delivery of Functional Peptides and Proteins," *Curr. Opin. Chem. Biol.* 3:89-94 (1999).

Haynes, B.F., "Scientific and Social Issues of Human Immunodeficiency Virus Vaccine Development," *Science* 260:1279-1286 (1993).

Hearn, M.T.W., et al., "Applications of Novel Affinity Cassette Methods: Use of Peptide Fusino Handles for the Purification of Recombinant Proteins," *J. Mol. Recognit.* 14:323-369 (2001).

Hedstrom, R., et al., "A Major Immunogen in *Schistosoma mansoni* Infections is Homologous to the Heat-Shock Protein Hsp70," *J. Exp. Med.* 165:1430-1435 (1987).

Hinuma, S., et al., "A Novel Strategy For Converting Recombinant Viral Protein Into High Immunogenic Antigen," *FEBS Lett.* 288(1,2):138-142 (Aug. 1991).

Hogervorst, E.M., et al., "Efficient Recognition by Rat T Cell Clones of an Epitope of Mycobacterial hsp 65 Inserted in *Escherichia coli* Outer Membrane Protein PhoE," *Eur. J. Immunol.* 20:2763-2768 (1990).

Horwitz, M.A., et al., "Protective Immunity Against Tuberculosis Induced by Vaccination With Major Extracellular Proteins of Mycobacterium tuberculosis," *Microbiology* 92:1530-1534 (Feb. 1995).

Horwitz, M.S., et al., "Diabetes induced by Coxsackie virus: Initiation by bystander damage and not molecular mimicry ," *Nature Med.* 4:781-785 (1998).

Huang, Q., et al., "In Vivo Cytotoxic T Lymphocyte Elicitation by Mycobacterial Heat Shock Protein 70 Fusion Proteins Maps to a Discrete Domain and Is CD4+ T Cell Independent," *J. Exp. Med.* 191(2):403-408 (Jan. 17, 2000).

Hudson, C.N., et al., "Active Specific Immunotherapy for Ovarian Cancer," *The Lancet*, 2:877-879 (Oct. 23, 1976).

Hughes, L.E., et al., "A Study in Clinical Cancer Immunotherapy," *Cancer*, 26:269-278 (Aug. 1970).

Humphery, L.J., et al., "Adjuvant Immunotherapy for Melanoma," *J. Surg. Oncol.*, 25:303-305 (1984).

Hunt, C. and Calderwood, S., "Characterization and Sequence of a Mouse hsp70 Gene and Its Expression in Mouse Cell Lines," *Gene* 87:199-204 (1990).

Husson, R.N. and Young, R.A., "Genes for the major protein antigens of Mycobacterium tuberculosis: The etiologic agents of tuberculosis and leprosy share an immunodominant antigen," *Proc. Natl. Acad. Sci. USA*, 84:1679-1683 (1987).

Jacobs, et al., "Introduction of Foreign DNA into Mycobacteria Using a Shuttle Phasmid," *Nature*, 327(6122):532-535 (Jun. 1987).

Janeway, et al., *Immunobiology*, 5th Ed., 2001, Garland Publishing, sections 1-5 to 1-13 (10 pages).

Janvier, B., et al., "Immune Response to a Major Epitope of p24 During Infection with Human Immunodeficiency Virus Type 1 and Implications for Diagnosis and Prognosis," *J. Clin. Microbiol.* 29(3):488-492 (Mar. 1991).

Jarecki-Black, J.C., et al., "The Effect of BCG-Vaccine Upon Experimental Visceral Leishmaniasis in Hampsters," *Ann. Clin. Lab. Sci.*, 14:464-466 (1984).

Jarrett, W.F.H., et al., "Studies on Vaccination against Papillomaviruses: Prophylactic and Therapeutic Vaccination with Recombinant Structural Proteins," *Virology*, 184:33-42 (1991).

Jin, X.W., et al., "Bovine Serological Response to a Recombinant BPV-1 Major Caspid Protein Vaccine," *Intervirology* 31:345-354 (1990).

Junda, S., "Heat Shock Proteins: Applications in health and disease," *Trends Biotechnol.*, 14(1):17-20 (1996).

Johnston, J.M., et al., "Antigenic and Immunogenic Properties of a Hepatitis A Virus Capsid Protein Expressed in *Escherichia coli*," *J. Infect. Dis.* 157(6):1203-1211 (Jun. 1988).

Jondal, M., et al., "MHC Class I-Restricted CTL Responses to Exogenous Antigens," *Immunity* 5:295-203 (Oct. 1996).

Kaufmann, S.H.E., et al., "Enumeration of T cells reactive with Mycobacterium tuberculosis organisms and specific for the recombinant mycobacterial 64-kDa protein," *Eur. J. Immunol.* 17:351-357 (1987).

Kazura, J.W., et al., "Protective Efficacy of a Cloned *Brugia malayi* Antigen in a Mouse Model of Microfilaremia," *J. Immunol.* 145(7):2260-2264 (Oct. 1990).

Kimmig, P. and Wenk, P., "Suppression of Parasitaemia from *Litomosoides carinii* by Immunisation with BCG and Microfilariae," *Z Parasitenkd*, 67:317-327 (1982).

Kit, M., et al., "Bovine Herpesvirus-1 (Infections Bovine Rhinotracheitis Virus)-Based Viral Vector Which Expresses Foot-and-Mouth Disease Epitopes," *Vaccine* 9: 564-572 (Aug. 1991).

Klinkert, M., et al., "Surface Proteins of *Mycoplasma hyopneumoniae* Identified from an *Escherichia coli* Expression Plasmid Library," *Infect. Immun.* 49(2): 329-335 (1985).

Knapp, B., et al., "A Histdin Alanine Rich Recombinant Antigen Protects Aotus Monkeys from *P. falciparium* Infection," *Behring Inst. Mitt.* 82:349-359 (1988).

Kol, A., et al., "Chlamydial and Human Heat Shock Protein 60s Activate Human Vascular Endothelium, Smooth Muscle Cells, and Macrophages," *J. Clin. Invest.* 103:571-577 (1999).

Könen-Waisman, S. et al., "Self Heat-Shock Protein (hsp60) Peptide Serves in a Conjugate Vaccine against a Lethal Pneumococcal Infection," *J. Infect. Dis.* 179:403-413 (1999).

Könen-Waisman, S. et al., "Self and Foreign 60 Kilodation Heat Shock Protein T Cell Epitope Peptides Serve As Immunogenic Carriers for a T Cell-Independent Sugar Antigen," *J. Immunol.*, 154:5977-5985 (1995).

Krska, J., et al., "Monoclonal Antibody Recognition and Function of a DnaK (HSP70) Epitope Found in Gram-Negative Bacteria," *J. Bacteriol* 175(20):6433-6440 (1993).

Krzych, U., et al., "Repertories of T Cells Directed Against A Large Protein Antigen, -Galactosidase," *J. Immunol.* 128(4):1529-1534 (Apr. 1982).

La Thangue, N.B. and Latchman, D.S., "A Cellular Protein Related to Heat-Shock Protein 90 Accumulates during Herpes Simplex Virus Infection and Is Overexpressed in Transformed Cells," *Exp. Cell Res.*, 178:169-179 (1988).

Lamb, F.I., et al., "Heterologous Expression of the 65-Kilodalton Antigen of *Mycobacterium leprae* and Murine T-Cell Responses to the Gene Product," *Infect. Immun.* 56(5):1237-1241 (May 1988).

Lamb, J.R., et al., "Stress Proteins May Provide a Link Between the Immune Response to Infection and Autoimmunity," *Int. Immun.*, 1(2): 191-196 (1989).

Lamb, J.R., et al., "Mapping of T Cell Epitopes Using Recombinant Antigens and Synthetic Peptides," *EMBO J.* 6(5):1245-1249 (1987).

Lawrence, R.M., et al., "Expression of the Cloned Gene for Enterotoxin Stb of *Escherichia coli*," *Infect. Immun.*, 58(4):970-977 (1990).

Layton, et al., "Induction of HIV-Specific Cytotoxic . . . ," *J. Immunol.* 151(2):1097-1107 (Jul. 1993).

Leclerc, C., et al., "A Synthetic Vaccine Constructed by Copolymerization of B and T Cell Determinants," *Eur. J. Immunol.* 17:269-273 (1987).

Lee, A.C.J., et al., "A Method for Preparing β-hCG Cooh Peptide-Carrier Conjugates of Predictable Composition," *Mol. Immunol.*, 17:749-756 (1980).

Lehner, T., et al., "Heat Shock Proteins Generate ?-Chemokines Which Function as Innate Adjuvants Enhancing Adaptive Immunity," *Eur. J. Immunol.* 30:594-603 (2000).

Lehner, T., et al., "Identification of T- and B-CellEpitopes in Synthetic Peptides Derived From a Streptococcus Mutans Protein and Characterization of Their Antigenicity and Immunogenicity," *Archs Oral Biol.* 35, Suppl.:39S-45S (1990).

Li, Z. and Srivastava, P.K., "Tumor Rejection Antigen gp96/grp94 is an ATPase: Implications for Protein Folding and Antigen Presentation," *EMBO J.*, 12(8):3143-3151 (1993).

Lindgren, M., et al., "Cell-Penetrating Peptides," *TIBS* 21(3):99-103 (Mar. 2000).

Lindquist, S. and Craig, E.A., "The Heat-Shock Proteins," *Annu. Rev. Genet.*, 22:631-677 (1988).

Lindquist, S., "The Heat-Shock Response," *Annu. Rev. Biochem.*, 55:1151-1191 (Jul. 1986).

Linsley, P.S., et al., "T-Cell Antigen CD28 Mediates Adhesion With B Cells By Interacting With Activation Antigen B7/BB-1," *Proc. Natl. Acad. Sci. USA* 87:5031-5035 (Jul. 1990).

Liu, H., et al., Abstract Th25.22 in *Clin. Invest. Med.* 27:73D (2004).

Löwenadler, B., et al., "T and B Cell Responses To Chimeric Proteins Containing Heterologous T Helper Epitopes Inserted At Different Positions," *Mol. Immunol.* 29(10):1185-1190 (1992).

Löwenadler, B., et al., "Enhanced Immunogenicity of Recombinant Peptide Fusions Containing Multiple Copies of Heterologous T Helper Epitope," *Eur. J. Immunol.* 20:1541-1545 (1990).

Löwenadler, B., et al., "A recombinant *Escherichia coli* heat-stable enterotoxin (Sta) fusion protein eliciting anti-STa neutralizing antibodies," *FEMS Microbiol. Lett.*, 82:271-277 (1991).

Lussow, A.R., et al., "Mycobacterial heat-shock proteins as carrier molecules", *Eur. J. Immunol.*, 21:2297-2302 (1991).

Matthews, R.C., et al., "Autoantibody to Heat-Shock Protein 90 Can Mediate Protection Against Systemic Candidosis," *Immunology* 74:20-24 (1991).

McCulloch, P.B., et al., "Recurrent Malignant Melanoma: Effect of Adjuvant Immunotherapy on Survival," *Can. Med. Assoc. J.*, 117:33-36 (Jul. 1977).

McKenzie, K.R., et al., "Sequence and Immunogenicity of the 70-kDa Heat Shock Protein of *Mycobacterium leprae*," *J. Immunol.* 147(1):312-319 (Jul. 1991).

Mehram V., et al., "Efficient Mapping of Protein Antigenic Determinants," *Proc. Natl. Acad. Sci. USA* 83:7013-7017 (Sep. 1986).

Merrick, R.M., et al., "The Use of -Galactosidase Fusiono Proteins Encoding the Early Region 1 Transforming Proteins of Adenovirus Type 12 to Examine the Humoral Response in Tumor-Bearing Animals," *J. Gen. Virol.* 72:955-960 (1991).

Miller, G.A., et al., "Characterization and Vaccine Potential of a Novel Recombinant Coccidial Antigen," *Infect. Immun.*, 57(7):2014-2020 (1989).

Miller, A., et al., "Immunotherapy in autoimmune diseases," *Curr. Opin. Immunol.*, 3:936-940 (1991).

Moore, S.K., et al., "Murine 86- and 84-kDa Heat Shock Proteins, cDNA Sequences, Chromosome Assignments, and Evolutionary Origins," *J. Biol. Chem.* 264(10):5343-5351 (1989).

More, et al., "Activation of Cytotoxic T Cells In Vitro . . . ," *Immunol. Lett.* 69:275-282 (1999).

Morgan, D.O., et al., "Protection of Cattle and Swine Against Foot-and-Mouth Disease, Using Biosynthetic Peptide Vaccines," *Am. J. Vet. Res. 51*(1):40-45 (Jan. 1990).

Morimoto, R.I., "Cells in Stress: Transcriptional Activation of Heat Shock Genes," *Science* 259:1409-1410 (Mar. 1993).

Morris, M.C., et al., "Translocating Peptides and Proteins and Their Use for Gene Delivery," *Curr. Opin. Biotechnol.* 11(5):461-466 (Oct. 2000).

Moser, D., et al., "The Humoral Response to Heat Shock Protein 70 in Human and Murine *Schistosomiases mansoni*," *Parasite Immunol.* 12:341-352 (1990).

Multhoff, G., et al., "The Role of Heat Shock Proteins in the Stimulation of an Immune Response," *Biol. Chem.* 379:295-300 (Mar. 1998).

Murphy, J.R. and Lefford, M.J., "Host Defenses in Murine Malaria: Induction of a Protracted State of Immunity with a Formalin-Killed *Plasmodium berghei* Blood Parasite Vaccine," *Infect. Immun.*, 22:798-803 (1978).

Murraym D.R., et al., "Viral Oncolysate in the Management of Malignant Melanoma, II. Clinical Studies"9 *Cancer*, 40:680-686 (Aug. 1977).

Myers, "Role of B Cell Antigen Processing and Presentation in the Humoral Immune Response," *FASEB J.* 5:2547-2553 (1991).

Nadler, S.G., et al., "Interaction of the Immunosupressant Deoxyspergualin with a Member of the Hsp70 Family of Heat Shock Proteins," *Science*, 258:484-486 (1992).

Nair, S., et al., "Calreticulin Displays In Vivo Peptide-Binding Activity and Can Elicit CTL Responses Against Bound Peptides," *J. Immunol.* 162:6426-6432 (1999).

NCBI Accession CAD93221, Probable Chaperone Protein DNAK . . . , Apr. 2005.

NCBI Accession NP_854111, 60 KDA Chaperonin . . . , Apr. 2005.

Noll, A. and Autenrieti, I.B., "Immunity against *Yersinia enterocolitica* by Vaccination with Yersinia HSP60 Immunostimulating Complexes or Yersinia HSP60 plus Interleukin-12," *Infect. Immun.*, 64:2955-2961 (1996).

Nov. 2000 Printout of a Web Page of Stressgen Biotechnologies (http//stressgen.com).

Oberg, L.A., et al., "Bacterially Expressed Nucleoprotein of Infectious Hematopoietic Necrosis Virus Augments Protective Immunity Induced by the Glycoprotein Vaccine in Fish," *J. Viro.* 65:4486-4489 (Aug. 1991).

Oettgen, H.F. and Old, L.J., "Chapter 6: The History of Cancer Immunotherapy." In *Biologic Therapy of Cancer*, DeVita, V.T., Hellman, S. and Rosenberg, S.A., eds., (London: J.B. Lippincott) pp. 98-103 (1991).

Oftung, et al., "Mapping of Mutiple HLA Class II-Restricted T-Cell Eptiopes of the Mycobacterial 70-Kilodalton Heat Shock Protein," *Infect. Immun.*, 62(12):5411-5418 (1994).

Oftung, F., et al., "Human T Cell Clones Recognize Two Abundant Mycobacterium tuberculosis Protein Antigens Expressed in *Escherichia coli*," *J. Immunol.* 138(3):927-931 (Feb. 1987).

Owens, T., et al., "The Cell Biology of T-dependent B Cell Activation," Leucocytes: Functions and Pathogenesis, Biochem. *Cell Biol.* 67:481-489 (1989).

Palladino, M.A., et al., "Expression of a Shared Tumor-Specific Antigen by Two Chemically Induced BALB/c Sarcomas," *Cancer Res.*, 47:5074-5079 (Oct. 1987).

Palliser, D., et al., "Multiple Intracellular Routes in the Cross-Presentation of a Soluble Protein by Murine Dendritic Cells," *J. Immunol.* 174:1879-1887 (2005).

Parker, "T-Cell Dependent B Cell Activation," *Annu. Rev. Immunol.* 11:331-360 (1993).

Rossi-Campos, A., et al., "Immunization of pigs against Actinobacillus pleuropneumoniae with two recombinant protein preparations," *Vaccine*, 10(8):512-518 (1992).

Rost, B., "Twilight Zone of Protein Sequence Alignments," *Protein Eng.* 12(2):85-94 (1999).

Rothbard, J.B., et al., "A Sequence Pattern Common to T Cell Epitopes," *EMBO J.* 7(1):93-100 (1988).

Sad, S., et al., "Bypass of Carrier-Induced Epitope-Specific Suppression Using a T-Helper Epitope," *Immunology* 76, 599-603 (1992).

Sakai, et al., "The Human -Fetoprotein Gene," *Biol. Chem.*, 260(5):5055-5060 (Apr. 1985).

Salgaller, et al., "Baculovirus Recombinants Expressing the Human Carcinoembryonic Antigen Gene," *Cancer Res.*, 53(9):2154-2161 (May 1993).

Schild, H., et al., "Stress Proteins and Immunity Mediated by Cytotoxic T Lymphocytes," *Curr. Opin. Immunol.* 11:109-113 (1999).

Schödel, F., et al., "Synthesis in Vibrio cholerae and Secretion of Hepatitis B Virus Antigens Fused to *Escherichia coli* Heat-Labile Entertoxin Subunit B," *Gene* 99:255-259 (1991).

Schoenberger, S.P., et al., "T-cell Help for Cytotoxic T Lymphocytes is Mediated by CD40-CD40L Interactions," *Nature* 393:480-483 (Jun. 4, 1998).

Schwarze, S.R., et al., "Protein Transduction: Unrestricted Delviery Into All Cells?," *Trends Cell Biol.* 10(7):290-295 (Jul. 2000).

Shaw, M.W., et al., "New Aspects of Influenza," *Clin. Microbiol. Rev.* 5(1):74-92 (1992).

Shinnick, et al., "The Mycobacterium tuberculosis 65-Kilodalton Antigen Is a Heat Shock Protein Which Corresponds to Common Antigen and to the *Escherichia coli* GroEL Protein," *Infect. Immun.*, 56(2):446-451 (Feb. 1988).

Shinnick, T.M., et al., "The Etiologic Agents of Leprosy and Tubeculosis Share an Immunoreactive protein Anitgen with the Vaccine Strain *Mycobacterium bovis* BCG," *Infect. Immun.*, 55(8):1932-1935 (1987).

Silverstein, A.M., "The History of Immunology," In *Fundamental Immunology, 2nd Edition*, Paul, W.E., ed., (NY:Raven Press), pp. 21, 23-24 (1989).

Smith, D.B., et al., "Mr 26,000 antigen of *Schistosoma japonicum* recognized by resistant WEHI 129/J mice is a parasite glutathione S-transferase," *Proc. Natl. Acad. Sci. USA* 83:8703-8707 (1986).

Snapper, et al., "Lysogeny and Transformation in Mycobacteria: Stable Expression of Foreign Genes," *Proc. Natl. Acad. Sci. USA*, 85(18):6987-6991 (Sep. 1988).

Sparks, F.C., et al., "Immunology and Adjuvant Chemoimmunotherapy of Breast Cancer," *Arch Surg*, 111:1057-1062 (Oct. 1976).

Spencer, J.C., et al., "Nonspecific Protection of Mice against Influenza Virus Infection by Local or Systemic Immunization with Bacille Calmette-Guérin," *J. Infect. Dis.*, 126:171-175 (1977).

Spindler, K.R., et al., "Analysis of Adenovirus Transforming Proteins from Early Regions 1A and 1B with Antisera to Inducible Fusion Antigens Produced in *Escherichia coli*," *J. Virol.* 49(1):132-141 (Jan. 1984).

Srivastava, P.K., and Das, M.R., "The Serologically Unique Cell Surface Antigen of Zajdela Ascitic Hepatoma is Also Its Tumor-Associated Transplantation Antigen," *Int. J. Cancer*, 33:417-422 (1984).

Srivastava, P.K. and Old, L.J., "Individually Distinct Transplantation Antigens of Chemically Induced Mouse Tumors," *Immunology Today*, 9:78-83 (Mar. 1988).

Srivastava, P.K. and Maki, R. G., "Stress-Induced Proteins in Immune Response to Cancer," *Curr. Top. Microbiol. Immunol.*, 167:109-123 (1991).

Srivastava, P.K., et al., "Tumor Rejection Antigens of Chemically Induced Sarcomas of Inbred Mice," *Proc. Natl. Acad. Sci., USA*, 83:3407-3411 (May 1986).

Srivastava, P.K. and Udono, H., "Heat Shock Protein-Peptide Complexes in Cancer Immunotherapy," *Curr. Opin. Immunol.*, 6:728-732 (1994).

Ståhl, S., et al., "A Dual Expression System for the Generation, Analysis and Purification of Antibodies to a Repeated Sequence of the *Plasmodium falciparum* Antigen Pf155/RESA," *J. Immunol. Methods* 124:43-52 (1989).

Sturrock, R.F., et al., "Attempts to Induce Resistance to *Schistosoma mansoni* and *S. haematobium* in Kenyan Baboons (*Papio anubius*) Using Non-Specific Immunostimulants," *Parasitology*, 90:101-110 (1985).

Su, G., et al., "Extracellular export of Shiga toxin B-subunit/haemolysin A (C-terminus) fusion protein expressed in *Salmonella typhimurium* aroA-mutant and stimulation of B-subunit specific antibody responses in mice," *Microb. Pathog.*, 13:465-476 (1992).

Suto, R. and Srivastava, P.K., "A Mechanism for the Specific Immunogenicity of Heat Shock Protein-Chaperoned Peptides," *Science* 269:1585-1588 (Sep. 15, 1995).

Suzue, K. and Young, R.A., "Adjuvant-Free hsp70 Protein System Elicits Humoral and Cellular Immune Responses to HIV-1 p24," *J. Immunol.* 156:873-879 (1996).

Suzue, K., et al., "Heat Shock Fusion Proteins As Vehicles For Antigen Delivery Into The Major Histocompatibility Complex Class I Presentation Pathway," *Proc. Natl. Acad. Sci. USA* 94:13146-13151 (Nov. 1997).

Suzue, K., et al., "Heat Shock Proteins as Immunological Carriers and Vaccines," *Stress-Inducible Cellular Responses* (U. Feige, R. I. Morimoto, I. Yahara, B. S. Polla, eds.), Birkhauser/Springer, 77: 451-465 (1996).

Talwar, G.P., et al. "Enhancement of antigonadotropin response to the -subunit of ovine luteinizing hormone by carrier conjugation and combination with the -subunit of human chorionic gonadotropin," *Fertil. Steril.*, 46(1):120-126 (1986).

Tamura, Y., et al., "Immunotherapy of Tumors with Autologous Tumor-Derived Heat Shock Protein Preparations," *Science* 278:117-120 (Oct. 3, 1997).

Tao, et al., "Idiotype/Granulocyte-Macrophage Colony-Stimulating Factor Fusion Protein as a Vaccine for B-Cell Lymphoma," *Nature*, 362(6422):755-758 (Apr. 1993).

Tetzlaff, C.L., et al., "Induction of Proliferative Responses of T Cells from Babesia bovis-Immune Cattle with a Recombinant 77-Kilodalton Merozoite Protein (Bb-1)," *Infect. Immun.*, 60(2):644-652 (1992).

Thanavala, Y.M., et al., "Affinity, cross-reactivity and biological effectiveness of rabbit antibodies against a synthetic 37 amino acid C-terminal peptide of human chorionic gonadotrophin," *Clin. Exp. Immunol.*, 39:112-118 (1980).

Thole, J.E.R., et al., "Use of Recombinant Antigens Expressed in *Escherichia coli* K-12 To Map B-Cell and T-Cell Epitopes on the Immunodominant 65-Kilodalton Protein of *Mycobacterium bovis* BCG," *Infect. Immun.* 56(6):1633-1640 (Jun. 1988).

Thole, J.E.R., et al., "Antigenic relatedness of a strongly immunogenic 65 kDa mycobacterial protein antigen with a similarly sized ubiquitous bacterial common antigen," *Microb. Pathog.*, 4:71-83 (1988).

Thole, J.E.R., et al., "Characterization, Sequence Determination, and Immunogenicity of a 64-Kilodalton Protein of *Mycobacterium bovis* BCG Expressed in *Escherichia coli* K-12," *Infect. Immunol.*, 55(6):1466-1475 (1987).

Tommassen, J., et al., "Molecular Analysis of the Promoter Region of the *Escherichia coli* K-12 phoE Gene—Identification of an Element, Upstream from the Promoter, Required for Efficient Expression of PhoE Protein," *Mol. Biol.* 198:633-641 (1987).

Townsend, et al., "Antigen Recognition by Class I-Restricted T Lymphocytes," *Ann. Rev. Immunol.* 7:601-624 (1989).

Traversari, C., et al., "A Nonapeptide Encoded by Human Gene MAGE-1 Is Recognized on HLA-A1 by Cytolytic T Lymphocited Directed Against Tumor Antigen MZ2-E," *J. Exp. Med.* 176:1453-1457 (1992).

Udono, H., et al., "Cellular Requirements For Tumor-Specific Immunity Elicited By Heat Shock Proteins: Tumor Rejection Antigen gp96 Primes CD8+ T Cells in vivo", *Proc. Natl. Acad. Sci. USA 91*:3077-3081 (Apr. 1994).

Udono, H., et al., "Comparison of Tumor-Specific Immunogenicities of Stress-Induced Proteins gp96, hsp90, and hsp70," *J. Immunol.* 152: 5398-5403 (Jun. 1994).

Udono, H. and Srivastava, P.K., "Heat Shock Protein 70-associated Peptides Elicit Specific Cancer Immunity," *J. Exp. Med.*, 178:1391-1396 (Oct. 1993).

Ullrich, S.J., et al., "A Mouse Tumor-Specific Transplantation Antigen is a Heat Shock-Related Protein," *Proc. Natl. Acad. Sci.*, USA, 83:3121-3125 (May 1986).

Ullrich, S.J., et al., "Transcriptional and Translational Analysis of the Murine 84- and 86-kDa Heat Shock Proteins," *J. Biol. Chem.* 264(12):6810-6816 (1989).

van Eden, W., et al., "Cloning of the mycobacterial epitope recognized by T lynmphocytes in adjuvant arthritis," *Nature*, 331(14):171-173 (1988).

Verdegaal, E.M.E. et al., "Heat Shock Protein 65 Induces CD62e, CD106, and CD54 on Cultured Human Endothelial Cells and Increases Their Adhesiveness for Monocytes and Granulocytes," *J. Immunol.*, 157:369-376 (1996).

Vodkin, M.H. and Williams, J.C., "A Heat Shock Operon in *Coxiella burnetii* Produces a Major Antigen Homologous to a Protein in Both Mycobacteria an *Escherichia coli*," *J. Bacteriol.*, 170(3):1227-1234 (1988).

Voellmy, et al., "Isolation and Functional Analysis . . . ," *PNAS*, 82:4949-4953 (1985).

Vogt, G., et al., "An Assessment of Amino Acid Exchange Matrices In Aligning Protein Sequences: The Twilight Zone Revisited," *J. Molec. Biol.* 249:816-831 (1995).

Vreden, S.G.S., et al., "Phase I Clinical Trial of a Recombinant Malaria Vaccine Consisting of the Circumsporozoite Repeat Region of Plasmodium Falciparum Coupled to Hepatitis B Surface Antigen" *Am. J. Trop. Med. Hyg.*, 45(5):533-538 (1991).

Walker, et al., "Escape From the Immune System," *Nature 407*:313-314 (2000).

Wang, T., et al., "Identification of the Peptide Biding Domain of hsc70," *J. Biol. Chem.*, 268(35):26049-26051 (1993).

Welch, W.J., et al., "Biochemical Characterization of the Mammalian Stress Proteins and Identification of Two Stress Proteins as Glucose—and CA2+—Ionophore-regulated Proteins," *J. Biol. Chem.*, 258(11): 7102-7111 (1983).

Welch, W.J. and Feramisco, J.R., "Rapid Purification of Mammalian 70,000-Dalton Stress Proteins: Affinity of the Proteins for Nucleotides," *Mol. Cell. Biol.*, 3:1229-1237 (1985).

Welch, W.J. and Feramisco, J.R., "Purification of the Major Mammalian Heat Shock Proteins," *J. Biol. Chem. 257*(24):14949-14959 (1982).

Xu, L., et al., "Epitope Mapping and Characterization of the Infectious Hematopoietic Necrosis Virus Glycoprotein, Using Fusion Proteins Synthesized in *Escherichia coli*," *J. Virol.* 65(3):1611-1615 (Mar. 1991).

Yewdell, et al., "The Binary Logic of Antigen Processing and Presentation to T Cells," *Cell 62*:203-206 (1990).

Young, D.B., et al., "The 65kDa antigen of mycobacteria—a common bacterial protein?," *Immunol. Today*, 8(7-8):215-219 (1987).

Young, R.A., "Stress Proteins and Immunology," Annu. Rev. Immunol., 8:401-420 (1990).

Young, R.A., et al., "Genes for the major protein antigens of the leprosy parasite *Mycobacterium leprae*," Nature, 316:450-452 (1985).

Young, D., et al., "Stress proteins are immune targets in leprosy and tuberculosis," *Proc. Natl. Acad. Sci. USA*, 85:4267-4270 (1988).

Zavala, F., et al., "Synthetic Peptide Vaccine Confers Protection Against Murine Malaria," *J. Exp. Med.*, 166:1591-1596 (1987).

Zhu, Z., et al., "Structural Analysis of Substrate Binding by the Molecular Chaperone DnaK," *Science 272*:1606-1614 (Jun. 14, 1996).

Zylicz, M., et al., "The grpE Protein of *Escherichia coli*," *J. Biol. Chem.*, 262(36):17437-17442 (1987).

Zylicz, M. and Georgopoulos, C., "Purification and Properties of the *Escherichia coli* dnaK Replication Protein," *J. Biol. Chem. 259*(14):8820-8825 (1984).

Li, et al., "Generation of Murine CTL by a Hepatitis B Virus-Specific Peptide and Evaluation of the Adjuvant Effect of Heat Shock Protein Glycoprotein 96 and Its Terminal Fragments," *Journal of Immunology 174*(1):195-204 (2005).

Stover, C.K., et al., "New Use of BCG for Recombinant Vaccines", *Nature*, 351:456-460 (1991).

Davis, B.D., et al., *Microbiology, second edition*, Harper & Row, Publishers, pp. 600 & 622 (1973).

Decision Revoking European Patent EP-B-0419569 (2001).

Doherty, et al., Evasion of host immune responses by tumours and viruses, "Vaccines against virally induced cancers", Wiley, Chichester (Ciba Foundation Symposium 187), pp. 245-260. See p. 245, Abstract (1994).

European Patent No. 0700445 B1; Opposition By Antigenics, Inc.: Statement of Grounds of Opposition (2002).

Hird, et al., *Immunotherapy with Monoclonal Antibodies, Genes and Cancer*, Edited by Carney, et al., pp. 183-189, see p. 185, first paragraph (1990).

Partidos, C.D., et al., "Immune Responses in Mice Following Immunization With Chimeric Synthetic Peptides Representing B and T Cell Epitopes of Measles Virus Proteins," *J. Gen. Virol. 72*1293-1299 (1991).

Pedersen, J., et al., "Removal of B-Terminal Polyhistidine Tags from Recombinant Proteins Using Engineered Aminopeptidases," *Protein Exp. Purif. 15*:389-400 (1999).

Peeters, J.M., et al., "Comparison of four bifunctional reagents for coupling peptides to proteins and the effect of the three moieties on the immunogenicity of the conjugates," *J. Immunol. Methods*, 120:133-143 (1989).

Phalipon, A., et al., "Expression of a poliovirus type 1 neutralization epitope on a diphtheria toxin fusion protein," *Vaccine*, 7:132-136 (1989).

Pinskey, C.M., et al., "Intravesical Administration of Bacillus Calmette-Guérin in Patients With Recurrent Superficial Carcinoma of the Urinary Bladder: Report of a Prospective, Randomized Trail," Cancer Treat. Rep., 69:47-53 (Jan. 1985).

Rambukkana, et al., "Identification and Characterization of Epitopes Shared Between the Mycobacterial 65-Kilodalton Heat Shock Protein and the Activity Secret Antigen 85 Complex: Their In Situ Expression on the Cell Wall Surface of *Mycobacterium leprae*," *Infect. Immun.*, 60(11):4517-4527 (Nov. 1992).

Rand, K.N., et al., "Cloning and Expression of a Protective Antigen from the Cattle Tick *Boophilus microplus*," *Plug. Natl. Acad. Sci. USA 86*:9657-9661 (Dec. 1989).

Raychaudhuri, S., et al., "Can Soluble Antigens Induce CD8$^+$ Cytotoxic T-Cell Responses? A Paradox Revisited," *Immunol. Today 14*344-348 (1993).

Rickard, M.D., "Cestode Vaccines," *Southeast Asian J. Trop. Med. Public Health*, 22: 287-290, 1991.

Rico, A.I., et al., "Characterization of the Immunostimulatory Properties of *Leishmania infantum* HSP70 by Fusion to the *Escherichia coli* Maltose-Binding Protein in Normal nu/nu BABL/c Mice," *Infect. Immun.* 66:347-352 (Jan. 1998).

Roman, E., et al., "Synthetic Peptides non-Covalently Bound to Bacterial hsp 70 Elicit Peptide-Specific T-Cell Responses in vivo," *Immunology 88*:487-492 (1996).

* cited by examiner

```
HUMP1    1,   MLRLPTVFRQMRPVSRVLAPHLTRAYAKDVKFGADARALMLQGVDLLADAVAVTMGPKGRTVIIEQSWGS   70,
                                                 ::    :::::  ::   ::::::::::::::
GROEL         ------------------------------MA-----AKDVKFGNDARVKMLRGVNVLADAVKVTLGPKGRNVVLDKSFGA  140,

HUMP1    71,  PKVTKDGVTVAKSIDLKDKYKNIGAKLVQDVANNTNEEAGDGTTTATVLARSIAKEGFEKISKGANPVEI  140,
              :: ::::::       :: :: :: : ::    ::  :  ::::::::::::::: :: :
GROEL         PTITKDGVSVAREIEPEDKFENMGAQMVKEVASKANDAAGDGTTTATVLAQAIITEGLKAVAAGMNPMDL  210,

HUMP1    141, RRGVMLAVDAVIAELKKQSKPVTTPEEIAQVATISANGDKEIGNIISDAMKKVGRKGVITVKDGKTLNDE  210,
              ::  :: :: ::   ::  :: :::::::::::: ::: :::   :: :: :::::::::::::::::
GROEL         KRGIDKAVTAAVEELKALSVPCSDSKAIAQVGTISANSDETVGKLIAEAMDKVGKEGVITVEDGTGLQDE  280,

HUMP1    211, LEIIEGMKFDRGYISPYFINTSKGQKCEFQDAYVLLSEKKISSIQSIVPALEIANAHRKPLVIIAEDVDG  280,
              :::::::::::::::::: :::::   :::::::::::::::: ::::::::::::::   ::::::::
GROEL         LDVVEGMQFDRGYLSPYFINKPETGAVELESPFILLADKKISNIREMLPVLEAVAKAGKPLLIIAEDVEG  350,

HUMP1    281, EALSTLVLNRLKVGLQVVAVKAPGFGDNRKNQLKDMAIATGGAVFGEEGLTLNLEDVQPHDLGKVGEVIV  350,
              :::::::: :: :::::::::::::::::::::::: ::::::   ::   ::: :  :::::::::
GROEL         EALATAVVNTIRGIVKVAAVKAPGFGDRRKAMLQDIATLTGGTVISEE-IGMELEKATLEDLGQAKRVVI  420,

HUMP1    351, TKDDAMLLKGKGDKAQIEKRIQEIIEQLDVTTSEYEKEKLNERLAKLSDGVAVLKVGGTSDVEVNEKKDR
              :::     ::: ::  :::  :::  ::::::: ::::::::::::: ::
GROEL         NKDTTTIIDGVGEEAAIQGRVAQIRQQIEEATSDYDREKLQERVAKLAGGVAVIKVGAATEVEMKEKKAR
```

Figure 2A

```
         421        430        440        450        460        470        480        490
HUMP1    VTDALNATRAAVEEGIVLGGGCALLRCIPALDSLTPANEDQKIGIEIIKRTLKIPAMTIAKNAGVEGSLI
         :::::::::::::::  :::  : :: :: :  :     ::  :: :       :  ::
GROEL    VEDALHATRAAVEEGVVAGGGVALIRVASKLADLRGQNEDQNVVSSSL--RAMEAPLRQIVLNCGEEPSVV 491        500        510        520        530        540        550        560
HUMP1    VEKIMQSSEVGYDAMAGDFVNMVEKGIIDPTKVVRTALLDAAGVASLLTTAEVVVTEIPKEEKDPGMGA
         ::    : ::  :  :  :      :::::::::: ::: :::::: ::      :::  :::  :  :
GROEL    ANTVKGGDGNYGYNAATEEYGNMIDMGILDPTKVTRSALQYAASVAGLMITTECMVTDLPKND-AADLGA 561        570
HUMP1    MGGMGG--GMGGGMF
         :::::: :  :::: :
GROEL    AGGMGGGMGGMGGMM--

Total score = 4667, 5 breaks
276 identities out of 545 possible matches between residues 25 random runs
Alignment score = 65.34   SD   Standard deviation = 18.94   Mean = 3429.48
```

Figure 2B

```
            10         20         30         40         50         60         70
             ,          ,          ,          ,          ,          ,          ,
HUMP1   MLRLPTVFRQMRPVSRVLAPHLTRAYAKDVKFGADARALMLQGVDLLADAVAVTMGPKGRTVIIEQSWGS
         ::                                   ::    :: :::::: ::          ::
ML65K   M------------------------------AKTIAYDEEARRGLERGLNSLADAVKVTLGPKGRNVLEKKWGA
            ,          ,          ,          ,          ,          ,          ,
            80         90        100        110        120        130        140

,          ,          ,          ,          ,          ,          ,
HUMP1   PKVTKDGVTVAKSIDLKDKYKNIGAKLVQDVANNTNEEAGDGTTTATVLARSIAKEGFEKISKGANPVEI
         : :::  :::: :::: :::  ::    :: :::::::::::::::::::::::::::
ML65K   PTITNDGVSIAKEIELEDPYEKIGAELVKEVAKKTDDVAGDGTTTATVLAQALVKEGLRNVAAGANPLGL
           150        160        170        180        190        200        210

,          ,          ,          ,          ,          ,          ,
HUMP1   RRGVMLAVDAVIAELKKQSKPVTTPEEIAQVATISANGDKEIGNIISDAMKKVGRKGVITVKDGKTLNDE
         ::  ::: :::::::  :::   ::::  :::    :: :: :::::   ::::::::::
ML65K   KRGIEKAVDKVTETLLKDAKEVETKEQIAATAAISA-GDQSIGDLIAEAMDKVGNEGVITVEESNTFGLQ
           220        230        240        250        260        270        280

,          ,          ,          ,          ,          ,          ,
HUMP1   LEIIEGMKFDRGYISPYFINTSKGQKCEFQDAYVLLSEKKISSIQSIVPALEIANAHRKPLVIIAEDVDG
         : :::::::::::: ::::::: :  :: :::: ::   ::::::::::::::::::::::: :::::
ML65K   LELTEGMRFDKGYISGYFVTDAERQEAVLEEPYILLVSSKVSTVKDLLPLLEKVIQAGKSLLIIAEDVEG
           290        300        310        320        330        340        350

,          ,          ,          ,          ,          ,          ,
HUMP1   EALSTLVLNRLKVGLQVVAVKAPGFGDNRKNQLKDMAIATGGAVFGEEGLTLNLEDVQPHDLGKVGEVIV
        ::::::: ::::::::::::::::::::::::::::::::::::  :: ::::::::::      ::::
ML65K   EALSTLVVNKIRGTFKSVAVKAPGFGDRRKAMLQDMAILTGAQVISEE-VGLTLENTDLSLLGKARKVVM
           360        370        380        390        400        410        420

,          ,          ,          ,          ,          ,          ,
HUMP1   TKDDAMLLKGKGDKAQIEKRIQEIIEQLDVTTSEYEKEKLNERLAKLSDGVAVLKVGGTSDVEVNEKKDR
         :::  ::: :: ::: :::::: :::::: :     ::::::::::::: ::::::          ::
ML65K   TKDETTIVEGAGDTDAIAGRVAQIRTEIENSDSDYDREKLQERLAKLAGGVAVIKAGAATEVELKERKHR
```

Figure 3A

```
              421,       430,       440,       450,       460,       470,       480,       490,
HUMP1         VTDALNATRAAVEEGIVLGGGCALLRCIPALDSLTPANEDQKIGIEIIKRTLKIPAMTIAKNAGVEGSLI
                ::         ::::: ::     :::: :              ::         ::   ::
ML65K         IEDAVRNAKAAVEEGIVAGGGVTLLQAAPALDKLKLTGDEAT-GANIVKVALEAPLRQIAFNSGMEPGVV 491,       500,       510,       520,       530,       540,       550,       560,
HUMP1         VEKIMQSSSEVGYDAMAGDFVNMVEKGIIDPTKVVRTALLDAAGVASLLTTAEVVVTEIPKEEKDPGMGA
                 ::  ::     ::         ::    ::::  :: ::: :  :: ::         :
ML65K         AEKVRNLSVGHGLNAATGEYEDLLKAGVADPVKVTRSALQNAASIAGLFTT-EAVVADKPEKTAAPASDP 561,       570,
HUMP1         MGGMGGGMGGGMF
                ::::: ::   :
ML65K         TGGMGG-MD---F

Total score = 4552, 7 breaks
255 identities out of 540 possible matches between residues 25 random runs
Alignment score = 47.73 SD   standard deviation = 23.86   Mean = 3413.16
```

Figure 3B

```
         10        20        30        40        50        60        70
         ,         ,         ,         ,         ,         ,         ,
HUMP1  MLRLPTVFRQMRPVSRVLAPHLTRAYAKDVKFGADARALMLQGVDLLADAVTMGPKGRTVIIEQSWGS
       ::                                   :: ::   ::      :: ::
TB65K  M------------------------------------AKTIAYDEEARRGLERGLNALADAVKVTLGPKGRNVVLEKKWGA 80        90       100       110       120       130       140
         ,         ,         ,         ,         ,         ,         ,
HUMP1  PKVTKDGVTVAKSIDLKDKYKNIGAKLVQDVANNTNEEAGDGTTTATVLARSIAKEGFEKISKGANPVEI
       :  :::: :  :: :: :  :       ::   :::::::::::::  ::::   :::
TB65K  PTITNDGVSIAKEIELEDPYEKIGAELVKEVAKKTDDVAGDGTTTATVLAQALRKEGLRNVAAGANPLGL 150       160       170       180       190       200       210
         ,         ,         ,         ,         ,         ,         ,
HUMP1  RRGVMLAVDAVIAELKKQSKPVTTPEEIAQVATISANGDKEIGNIIISDAMKKVGRKGVITVKDGKTLNDE
        ::  :   ::    ::::::::  ::  :::     ::::::: :      ::::  ::::::::
TB65K  KRGIEKAVEKVTETLLKGAKEVETKEQIAATAAISA-GDQSIGDLIAEAMDKVGNEGVITVEESNTFGLQ 220       230       240       250       260       270       280
         ,         ,         ,         ,         ,         ,         ,
HUMP1  LEIIEGMKFDRGYISPYFINTSKGQKCEFQDAYVLLSEKKISSIQSIVPALEIANAHRKPLVIIAEDVDG
       ::::::::::::::::::::  :::  ::::::::::  : :   ::::::  :::::::::::::::
TB65K  LELTEGMRFDKGYISGYFVTDPERQEAVLEDPYILLVSSKVSTVKDLLPLLEKVIGAGKPLLIIAEDVEG 290       300       310       320       330       340       350
         ,         ,         ,         ,         ,         ,         ,
HUMP1  EALSTLVLNRLKVGLQVVAVKAPGFGDNRKNQLKDMAIATGGAVFGEEGLTLNLEDVQPHDLGKVGEVIV
       ::::::: ::::                                ::                ::
TB65K  EALSTLVVNKIRGTFKSVAVKAPGFGDRRKAMLQDMAILTGGQVISEE-VGLTLENADLSLLGKARKVVV 360       370       380       390       400       410       420
         ,         ,         ,         ,         ,         ,         ,
HUMP1  TKDDAMLLKGKGDKAQIEKRIQEIIEQLDVTTSEYEKEKLNERLAKLSDGVAVLKVGGTSDVEVNEKKDR
       ::                                        ::          ::::
TB65K  TKDETTIVEGAGDTDAIAGRVAQIRQEIENSDSDYDREKLQERLAKLAGGVAVIKAGAATEVELKERKHR
```

Figure 4A

```
        421                                                                490
HUMP1   VTDALNATRAAVEEGIVLGGGCALLRCIPALDSLTPANEDQKIGIEIIKRTLKIPAMTIAKNAGVEGSLI
        ::   :::::::::  ::       ::                  ::            : :  :::
TB65K   IEDAVRNAKAAVEEGIVAGGGVTLLQAAPTLDELK-LEGDEATGANIVKVALEAPLKQIAFNSGLEPGVV 491       500       510       520       530       540       550       560
HUMP1   VEKIMQSSEVGYDAMAGDFVNMVEKGIIDPTKVVRTALLDAAGVASLLTTAEVVVTEIPKEEKDPGMGA
        ::   ::  :      ::       :: :: :    :::   ::  :::::      ::     :: :
TB65K   AEKVRNLPAGHGLNAQTGVYEDLLAAGVADPVKVTRSALQNAASIAGLFLTTEAVVADKPEKEKASVPG- 561       570
HUMP1   MGGMGGGMGGGMF
        ::  :::  ::
TB65K   ----GGDMGGMDF

Total score = 4560, 5 breaks
 257 identities out of 540 possible matches between residues 25 random runs
Alignment score =     49.36 SD    Standard deviation =   23.23     Mean = 3413.16
```

Figure 4B

SEQUENCE LISTING

```
<160> NUMBER OF SEQ ID NOS: 4

<210> SEQ ID NO 1
<211> LENGTH: 573
<212> TYPE: PRT
<213> ORGANISM: Unknown
<220> FEATURE:
<223> OTHER INFORMATION: Amino acid sequence of the human P1 protein

<400> SEQUENCE: 1

Met Leu Arg Leu Pro Thr Val Phe Arg Gln Met Arg Pro Val Ser Arg
 1               5                  10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
```

```
                225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 2
<211> LENGTH: 547
<212> TYPE: PRT
<213> ORGANISM: Unknown
<220> FEATURE:
<223> OTHER INFORMATION: Amino acid sequence of the groEL protein

<400> SEQUENCE: 2

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
```

-continued

```
                20                  25                  30
Pro Lys Gly Arg Asn Val Val Leu Asp Lys Ser Phe Gly Ala Pro Thr
             35                  40                  45
Ile Thr Lys Asp Gly Val Ser Val Ala Arg Glu Ile Glu Pro Glu Asp
 50                  55                  60
Lys Phe Glu Asn Met Gly Ala Gln Met Val Lys Val Ala Ser Lys
 65                  70                  75                  80
Ala Asn Asp Ala Ala Gly Asp Gly Thr Thr Thr Ala Thr Val Leu Ala
                 85                  90                  95
Gln Ala Ile Ile Thr Glu Gly Leu Lys Ala Val Ala Ala Gly Met Asn
                100                 105                 110
Pro Met Asp Leu Lys Arg Gly Ile Asp Lys Ala Val Thr Ala Ala Val
                115                 120                 125
Glu Glu Leu Lys Ala Leu Ser Val Pro Cys Ser Asp Ser Lys Ala Ile
                130                 135                 140
Ala Gln Val Gly Thr Ile Ser Ala Asn Ser Asp Glu Thr Val Gly Lys
145                 150                 155                 160
Leu Ile Ala Glu Ala Met Asp Lys Val Gly Lys Glu Gly Val Ile Thr
                165                 170                 175
Val Glu Asp Gly Thr Gly Leu Gln Asp Glu Leu Asp Val Val Glu Gly
                180                 185                 190
Met Gln Phe Asp Arg Gly Tyr Leu Ser Pro Tyr Phe Ile Asn Lys Pro
            195                 200                 205
Glu Thr Gly Ala Val Glu Leu Glu Ser Pro Phe Ile Leu Leu Ala Asp
        210                 215                 220
Lys Lys Ile Ser Asn Ile Arg Glu Met Leu Pro Val Leu Glu Ala Val
225                 230                 235                 240
Ala Lys Ala Gly Lys Pro Leu Leu Ile Ile Ala Glu Asp Val Glu Gly
                245                 250                 255
Glu Ala Leu Ala Thr Ala Val Val Asn Thr Ile Arg Gly Ile Val Lys
                260                 265                 270
Val Ala Ala Val Lys Ala Pro Gly Phe Gly Asp Arg Arg Lys Ala Met
                275                 280                 285
Leu Gln Asp Ile Ala Thr Leu Thr Gly Gly Thr Val Ile Ser Glu Glu
            290                 295                 300
Ile Gly Met Glu Leu Glu Lys Ala Thr Leu Glu Asp Leu Gly Gln Ala
305                 310                 315                 320
Lys Arg Val Val Ile Asn Lys Asp Thr Thr Thr Ile Ile Asp Gly Val
                325                 330                 335
Gly Glu Glu Ala Ala Ile Gln Gly Arg Val Ala Gln Ile Arg Gln Gln
                340                 345                 350
Ile Glu Glu Ala Thr Ser Asp Tyr Asp Arg Glu Lys Leu Gln Glu Arg
            355                 360                 365
Val Ala Lys Leu Ala Gly Gly Val Ala Val Ile Lys Val Gly Ala Ala
        370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Val Val Ala Gly Gly Gly
                405                 410                 415
Val Ala Leu Ile Arg Val Ala Ser Lys Leu Ala Asp Leu Arg Gly Gln
                420                 425                 430
Asn Glu Asp Gln Asn Val Val Ser Ser Leu Arg Ala Met Glu Ala
                435                 440                 445
```

```
Pro Leu Arg Gln Ile Val Leu Asn Cys Gly Glu Glu Pro Ser Val Val
    450                 455                 460

Ala Asn Thr Val Lys Gly Gly Asp Gly Asn Tyr Gly Tyr Asn Ala Ala
465                 470                 475                 480

Thr Glu Glu Tyr Gly Asn Met Ile Asp Met Gly Ile Leu Asp Pro Thr
                485                 490                 495

Lys Val Thr Arg Ser Ala Leu Gln Tyr Ala Ala Ser Val Ala Gly Leu
                500                 505                 510

Met Ile Thr Thr Glu Cys Met Val Thr Asp Leu Pro Lys Asn Asp Ala
            515                 520                 525

Ala Asp Leu Gly Ala Ala Gly Gly Met Gly Gly Met Gly Gly Met Gly
    530                 535                 540

Gly Met Met
545

<210> SEQ ID NO 3
<211> LENGTH: 540
<212> TYPE: PRT
<213> ORGANISM: Unknown
<220> FEATURE:
<223> OTHER INFORMATION: Amino acid sequence of the 65kDa M. leprae
      protein

<400> SEQUENCE: 3

Met Ala Lys Thr Ile Ala Tyr Asp Glu Glu Ala Arg Arg Gly Leu Glu
  1               5                  10                  15

Arg Gly Leu Asn Ser Leu Ala Asp Ala Val Lys Val Thr Leu Gly Pro
                 20                  25                  30

Lys Gly Arg Asn Val Val Leu Glu Lys Lys Trp Gly Ala Pro Thr Ile
             35                  40                  45

Thr Asn Asp Gly Val Ser Ile Ala Lys Glu Ile Glu Leu Glu Asp Pro
         50                  55

```
                    245                 250                 255
Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
            275                 280                 285

Asp Met Ala Ile Leu Thr Gly Ala Gln Val Ile Ser Glu Glu Val Gly
            290                 295                 300

Leu Thr Leu Glu Asn Thr Asp Leu Ser Leu Leu Gly Lys Ala Arg Lys
305                 310                 315                 320

Val Val Met Thr Lys Asp Glu Thr Thr Ile Val Glu Gly Ala Gly Asp
                    325                 330                 335

Thr Asp Ala Ile Ala Gly Arg Val Ala Gln Ile Arg Thr Glu Ile Glu
                340                 345                 350

Asn Ser Asp Ser Asp Tyr Asp Arg Glu Lys Leu Gln Glu Arg Leu Ala
            355                 360                 365

Lys Leu Ala Gly Gly Val Ala Val Ile Lys Ala Gly Ala Ala Thr Glu
            370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Thr
                    405                 410                 415

Leu Leu Gln Ala Ala Pro Ala Leu Asp Lys Leu Lys Leu Thr Gly Asp
            420                 425                 430

Glu Ala Thr Gly Ala Asn Ile Val Lys Val Ala Leu Glu Ala Pro Leu
                    435                 440                 445

Lys Gln Ile Ala Phe Asn Ser Gly Met Glu Pro Gly Val Val Ala Glu
            450                 455                 460

Lys Val Arg Asn Leu Ser Val Gly His Gly Leu Asn Ala Ala Thr Gly
465                 470                 475                 480

Glu Tyr Glu Asp Leu Leu Lys Ala Gly Val Ala Asp Pro Val Lys Val
                    485                 490                 495

Thr Arg Ser Ala Leu Gln Asn Ala Ala Ser Ile Ala Gly Leu Phe Thr
            500                 505                 510

Thr Glu Ala Val Val Ala Asp Lys Pro Glu Lys Thr Ala Ala Pro Ala
            515                 520                 525

Ser Asp Pro Thr Gly Gly Met Gly Gly Met Asp Phe
            530                 535                 540

<210> SEQ ID NO 4
<211> LENGTH: 540
<212> TYPE: PRT
<213> ORGANISM: Unknown
<220> FEATURE:
<223> OTHER INFORMATION: Amino acid sequence of the 65kDa M.
      tuberculosis protein

<400> SEQUENCE: 4

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60
```

```
Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                 85                  90                  95

Ala Leu Arg Lys Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
```

-continued

```
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540
```

STRESS PROTEINS AND USES THEREFOR

RELATED APPLICATIONS

This application is a continuation of U.S. application Ser. No. 10/880,771, filed Jun. 28, 2004, now abandoned, which is a continuation of U.S. application Ser. No. 10/046,649, filed Jan. 14, 2002, now abandoned, which is a divisional of U.S. application Ser. No. 08/336,251, filed Nov. 3, 1994, now U.S. Pat. No. 6,338,952 B1. The entire teachings of the above applications are incorporated herein by reference.

GOVERNMENT SUPPORT

Work described herein was funded by grants from the National Institutes of Health (AI23545), the World Health Organization Program for Vaccine Development, and the World Health Organization/World Bank/United Nations Development Program Special Program for Research and Training in Tropical Diseases. The United States government has certain rights in the invention.

BACKGROUND OF THE INVENTION

Although the function of stress proteins is not entirely clear, it appears that some participate in assembly and structural stabilization of certain cellular and viral proteins, and their presence at high concentrations may have an additional stabilizing effect during exposure to adverse conditions. Neidhardt, F. C. and R. A. Van Bogelen, In: *Escherichia coli* and *Salmonella typhimurium*, Cellular and Molecular Biology, (eds. Neidhardt, F. C., Ingraham, J. L., Low, K. B., Magasanik, B. Schaechter, M. and Umbarger, H. E. (Am. Soc. Microbiol., Washington, D.C.), pp. 1334-1345 (1987); Pelham, H. R. B. *Cell*, 46:959-961 (1986); Takano, T. and T. Kakefuda, *Nature*, 239:34-37 (1972); Georgopoulos, C. et al., *New Biology,* 239:38-41 (1972). Phagocytic host cells produce a hostile environment of foreign organisms, and the ability to produce stress proteins has been implicated in the survival of bacterial pathogens within macrophages Christman, M. F. et al., *Cell,* 41:753-762 (1985).

*Mycobacterium* (M.) *tuberculosis* and *Mycobacterium* (M.) *leprae* are the etiologic agents of tuberculosis and leprosy, respectively. These diseases afflict 20-30 million people and continue to present a significant global health problem. Joint International Union Against Tuberculosis and World Health Organization Study Group, *Tubercle,* 63:157-169 (1982); Bloom, B. and T. Godal, *Rev. Infect Dis.* 5:765-780 (1983). To develop more effective tools for the diagnosis and prevention of these diseases, it is important to understand the immune response to infection by mycobacterial pathogens.

The antibody and T-cell responses to infection or inoculation with killed mycobacteria have been studied in humans and in animals. Human patients with tuberculosis or leprosy produce serum antibodies directed against at least 12 mycobacterial proteins. Some of these proteins are also recognized by well-characterized murine monoclonal antibodies. Mice immunized with mycobacterial lysates produce antibodies that are directed predominantly to six *M. tuberculosis* and six *M. leprae* protein antigens. Engers, H. D. *Infect. Immun.,* 48:603-605 (1985); Engers, H. D., *Infect. Immun.,* 51:718-720 (1986). Genes encoding these 12 mycobacterial antigens have been cloned, and recombinant proteins produced from these clones have been used to investigate the human T-lymphocyte response to mycobacterial infection. Husson, R. N. and R. A. Young, *Proc. Natl. Acad. Sci., USA,* 84:1679-1683 (1987); Young, R. A. et al., *Nature,* 316:450-452 (1985); Britton, W. J. et al., *Lepr. Rev.,* 57, Suppl. 2, 67-75 (1986).

Protection against mycobacterial disease involves cell-mediated immunity. Joint International Union Against Tuberculosis and World Health Organization Study Group, *Tubercle,* 63:157-169 (1982); Hahn, H. and S. H. E. Kaufman, *Rev. Infect. Dis.,* 3:1221-1250 (1981). T-lymphocytes cloned from patients or from volunteers immunized with killed mycobacteria have been tested for their ability to recognize the recombinant mycobacterial proteins. Lymphocyte-proliferation assays demonstrate that most of the antigens identified with monoclonal antibodies are involved in the T-cell response to mycobacterial infection or vaccination in mice and in humans. Limiting dilution analysis indicates that 20% of the mycobacterial-reactive $CD4^+$ T-lymphocytes in mice immunized with *M. tuberculosis* recognize a single protein, the 65-kDa antigen. Kaufman, S. H. E. et al., *Eur. J. Immunol.,* 17:351-357 (1987).

SUMMARY OF THE INVENTION

The present invention relates to stress proteins and methods of modulating an individual's (such as a human, other mammal or other vertebrate) immune response. In particular, it relates to the use of such stress proteins in immune therapy or prophylaxis, which results in an induction or enhancement of an individual's immune response and as an immunotherapeutic agent which results in a decrease of an individual's response to his or her own cells. In the embodiment in which an individual's immune response is induced or enhanced, the induced or enhanced response can be a response to antigens, such as those derived from a pathogen or cancer cell, or can be upregulation of the individual's immune status, such as in an immune compromised individual. In immune prophylaxis, stress proteins are administered to prevent or reduce the effects in an individual of a pathogen, which can be any virus, microorganism, parasite or other organism or substance (e.g., a toxin or toxoid) which causes disease or to prevent or reduce the effects in an individual of cancer cells. In preventing or reducing adverse effects of pathogens which contain stress proteins (e.g., bacteria, parasite, fungus) according to the method of the present invention, an individual's immune response to the pathogen's stress protein(s) is induced or enhanced through the administration of a vaccine which includes the pathogen's stress protein(s) or other stress proteins. The stress protein can be administered alone, as a member or component of a conjugate (e.g., joined to another antigen by chemical or recombinant means such as joined to a fusion partner resulting in a fusion protein), or as an adjuvant or carrier molecule to enhance or obtain a desired immune response to an antigen.

The present invention also relates to compositions which are conjugates comprised of a stress protein joined to another substance or component. For example, the present invention relates to a conjugate in which a stress protein is chemically linked to an antigen, or in which a stress protein is fused to an antigen (e.g., a fusion protein).

The present invention also relates to a method of generating monoclonal or polyclonal antibodies to a substance using a conjugate comprised of a stress protein joined to the substance. In this embodiment, an effective amount of the conjugate (i.e., an amount which results in an immune response in the host) is introduced into a mammalian host which results in production of antibodies to the substance in the host. The antibodies are removed from the host and purified using known techniques (e.g., chromatography).

Preventing or reducing adverse effects of viral pathogens which do or do not contain stress proteins, as well as preventing or reducing the adverse effects of cancer cells according to the present method, is effected by enhancing an individual's immune surveillance system. Enhancement of immune response can be effected by modulating the immune cells by stimulation with a stress protein (e.g., a bacterial stress protein).

In the embodiment in which an individual's immune response is decreased, such as is used in treating autoimmune diseases, stress proteins known to be involved in the autoimmune response are administered to turn down an individual's immune response by tolerizing the individual to the stress proteins. Alternatively, the immune response to stress protein, which is known to occur in autoimmune disease, is reduced by interfering with the ability of immune cells which respond to stress proteins to do so.

A selected stress protein of the present invention can be administered to an individual, according to the method of the present invention, and result in an immune response which provides protection against subsequent infection by a pathogen (e.g., bacteria, other infectious agents which produce stress proteins) or reduction or prevention of adverse effects of cancer cells. Alternatively, a selected stress protein can be administered to an individual, generally over time, to induce immune tolerance against the selected stress protein. For example, a selected stress protein can be administered in multiple doses over time in order to induce immune tolerance against an autoimmune disease such as rheumatoid arthritis.

BRIEF DESCRIPTION OF THE DRAWINGS

FIGS. 2A-2B are a comparison of the amino acid sequence of the human P1 protein (573 residues) (SEQ ID NO: 1) and the amino acid sequence of the groEL protein (547 residues) (SEQ ID NO: 2).

FIGS. 3A-3B are a comparison of the amino acid sequence of the human P1 protein (573 residues) (SEQ ID NO: 1), which is a homolog of groEL protein, and the amino acid sequence of the 65 kDa *M. leprae* protein (540 residues) (SEQ ID NO: 3).

FIGS. 4A-4B are a comparison of the amino acid sequence of the human P1 protein (573 residues) (SEQ ID NO: 1), which is a homolog of the groEL protein, and the amino acid sequence of the 65 kDa *M. tuberculosis* protein (540 residues) (SEQ ID NO: 4).

DETAILED DESCRIPTION OF THE INVENTION

Figure 1A:
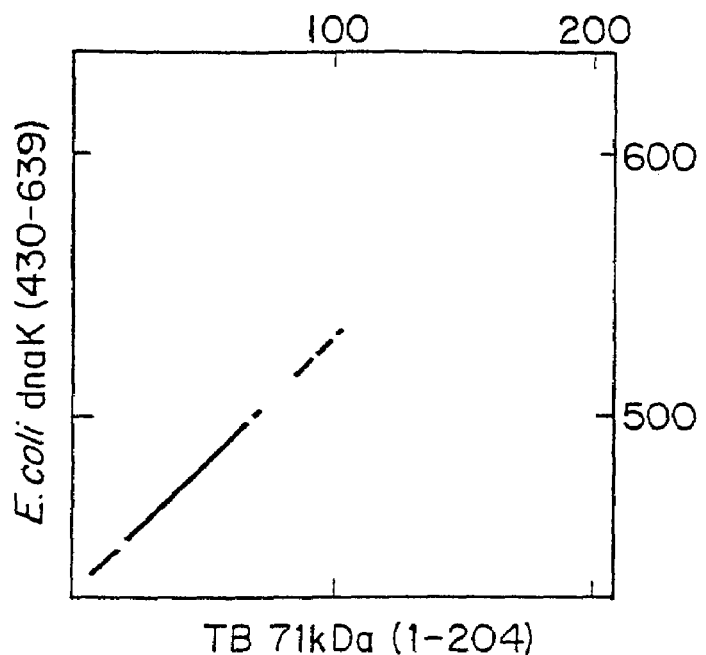
FIG. 1A is a graph illustrating the sequence similarity between portions of the *M. tuberculosis* 71-kDa antigen (residues 1-204; TB 71 kDa) and the *E. coli* DnaK protein (residues 430-639).

Cells respond to a variety of stressful stimuli by increasing the synthesis of specific stress proteins. The most extensively studied cellular response to stressful stimuli is the synthesis of heat shock proteins (hsp) by a cell, induced by a sudden increase in temperature. Because many of the heat shock proteins are also induced by other stresses, they are frequently called stress proteins. Stress proteins and their relatives appear to help assemble and disassemble protein complexes. In bacteria, the major stress proteins, hsp70 and hsp60, occur at moderate levels in cells that have not been stressed but accumulate to very high levels in stressed cells. For example, hsp70 and hsp60 normally account for 1-3% of total *E. coli* protein, but can accumulate to about 25% under stressful conditions. Eukaryotic hsp70 and hsp60 proteins do not accumulate to these extreme levels. Their levels range from undetectable to moderately abundant, depending on the organism and cell type.

The present invention is based on the observation that stress proteins are among the major antigens available for presentation to T lymphocytes and may be common immune targets in a broad spectrum of infectious diseases. Immune responses to stress proteins are involved in immune surveillance by the body and a variety of different T cell types has been shown to recognize highly conserved stress protein determinants. Several observations, described below, suggest a model of immune surveillance in which self-reactive T cells provide a first line of defense against infection or other invasion by pathogens, which include, but are not limited to, viruses, microorganisms, other organisms, substances such as toxins and toxoids, and agents which cause cell transformation, by recognizing and helping to eliminate stressed autologous cells, as well as cells infected with intracellular pathogens. Without wishing to be bound by this model, it is presented as one means by which it is possible to explain why prokaryotic and eukaryotic cells respond to a variety of potentially damaging stimuli, such as elevated temperature, by increasing the synthesis of a family of proteins, referred to as stress proteins, which are among the most highly conserved and abundant proteins found in nature.

Investigation of antigens involved in the immune response to the tuberculosis and leprosy bacilli (*M. tuberculosis* and *M. leprae*) initially led to the observation that a variety of stress proteins are among the major targets of the immune response, as is described at greater length below.

Further assessment has demonstrated that stress proteins may be common immune targets in a broad spectrum of infectious diseases. Sequence analysis has revealed 70-kDa heat shock protein homologues among major antigens of the protozoan parasites *Plasmodium falciparum* (Bianco, A. E. et al., *Proc. Natl. Acad. Sci., USA*, 83:8713-8717 (1986)) and *Schistosoma mansoni* (Hedstrom, R. et al., *J. Exp. Med.*, 165:1430-1435 (1987)) and the malarial parasite *Brugia malayi* (Selkirk, M. E. et al., *J. Cell Biochem.*, 12D:290 (1988)). Similarly, homologues of GroEL have been found among antigens involved in the immune response to *Salmonella typhimurium* and *Coxiella* (Vodkin, M. H. and J. C. Williams, *J. Bacteriol*, 170:1227 (1988)), as well as *Bordetella pertussis* (Del Giudice, G., et al., *J of Imm.*, 150: 2025-2032 (1993)). The presence of stress proteins among major immune targets in a variety of human pathogens is support for the idea that the stress response may be a general component of infection and that stress proteins should be considered among candidates for subunit vaccines. All organisms respond to heat by inducing synthesis of heat shock proteins (hsp), which are a group of proteins. This response is the most highly conserved genetic system known and has been shown to occur in every organism, including microorganisms, plants and animals, investigated to date. Many of the characteristics of the response are common to all organisms and the hsp are among the most highly conserved proteins known. For example, hsp90 family and hsp70 family proteins are present in widely diverse organisms. The proteins in each family— even in such diverse organisms—show approximately 50% identity at the amino acid level and at the nonidentical residues, exhibit many similarities. Several of the proteins induced by heat are also induced by a variety of other stresses. The hsps or a closely related/similar protein are present in all organisms at normal temperatures and have been shown to have key functions in normal cell metabolism. Lindquist, S. and E. A. Craig, *Ann. Rev. Genet.*, 22:631-677 (1988). Because the stress response is common to prokaryotes and eukaryotes and stress proteins are among the most highly conserved in sequence, it is reasonable to expect that an antigen from one pathogen could immunize against another pathogen. Exposure to foreign stress proteins early in life might, in fact, induce a degree a immunity to a variety of infectious agents. If so, this could provide an explanation for the observation that, for many pathogens, only a fraction of infected individuals actually acquire clinical disease.

The following is a description of the relationship which has been observed between stress proteins and the immune response to mycobacterial infection; of the observation and supporting information that stress proteins are immune targets in many infections by pathogens; of the role of stress proteins as immune targets in transformed cells; of recognition of the fact that the immune response to conserved stress protein determinants may play an important role in autoimmune pathology in rheumatoid arthritis, as well as in adjuvant arthritis; and of the role of stress proteins in immune surveillance, as well as a model proposed for immune surveillance in which self-reactive T cells provide a first line of defense against infection and cell transformation.

Mycobacterial Stress Proteins are Targets of the Immune Response

An intriguing relationship between stress proteins and the immune response to mycobacterial infection has been observed. A more detailed examination of stress protein determinants and immune response mechanisms is essential to understanding the relationship among stress proteins, infection, and immunity.

In view of the involvement of proteins of *M. tuberculosis* and *M. leprae* in humoral and cell-mediated immune responses and to establish the functions of these proteins in the mycobacterial cell, the DNA encoding several of the *M. tuberculosis* and *M. leprae* antigens have been sequenced. The results, discussed in Example 1, demonstrate that many of these mycobacterial protein antigens exhibit striking sequence similarity to known stress-induced proteins. Three of the *M. leprae* and two of the *M. tuberculosis* protein antigens studied have been shown to exhibit striking sequence similarity to known stress proteins. For reasons discussed in Example 1, it is concluded that two of the *M. leprae* and two of the *M. tuberculosis* antigens are homologues of the *E. coli* DnaK and GroEL proteins.

In mice, immunization with mycobacterial lysates elicits antibody responses to at least six *M. tuberculosis* protein antigens and a similar number of *M. leprae* protein antigens. Monoclonal antibodies specific for these proteins have been used to isolate clones from λgtll DNA expression libraries of *M. tuberculosis* and *M. leprae*. The sequence of the DNA clones revealed that mycobacterial hsp70 (alias 70 kDa antigen) and hsp60 (alias 65 kDa antigen, GroEL) were the major targets of the murine antibody response to both *M. tuberculosis* and *M. leprae*. Two additional hsp, an 18 kDa member of the small hsp family and a 12 kDa homologue of groES, were found among the *M. leprae* and *M. tuberculosis* antigens. Young, D. B., et al., *Proc. Natl. Acad. Sci., USA*, 85:4267-4270 (1988); Shinnick, T. M., et al., *Nuc. Acids Res.*, 17:1254 (1989).

The mycobacterial stress proteins are among the immunodominant targets of both murine antibody and T cell responses. In one study which summarized results obtained from 10 laboratories, a collection of 24 murine monoclonal antibodies recognized 6 *M. leprae* proteins; 7 of these antibodies are directed against 6 different determinants in the *M. leprae* hsp60. Engers, H. D., et al., *Infect. Immun.*, 48:603-605 (1985); Mehra, V., et al., *Proc. Natl. Acad. Sci., USA*, 83:7013-7017 (1986). In a similar study, 3 of 33 monoclonal antibodies raised against *M. tuberculosis* recognized the *M. tuberculosis* hsp60 protein. Engers, H. D., et al., *Infect. Immun.*, 51:718-720 (1986). Finally, limiting dilution analysis indicates that 20% of the mycobacterial-reactive CD4+ T lymphocytes in mice immunized with *M. tuberculosis* recognize this antigen. Kaufmann, S. H., et al., *Eur. J. Immunol.*, 17:351-357 (1987).

Although a rigorous quantitative analysis of the human immune response to mycobacterial stress proteins has not yet been reported, mycobacterial stress proteins are recognized by human antibodies and T lymphocytes and the evidence suggests that these proteins are among the major targets of the human cell mediated immune response. Emmrich. F., et al., *J. Exp. Med.*, 163:1024-1029 (1985); Mustafa, A. S., et al., *Nature* (London). 319:63-66 (1986); Oftung, F., et al., *J. Immunol.*, 138:927-931 (1987); Lamb, J. R., et al., *EMBO J*, 6:1245-1249 (1987). T lymphocytes from patients with mycobacterial infection or from volunteers immunized with mycobacteria have been cloned and tested for their ability to recognize the mycobacterial stress proteins. In each of these studies, some fraction of the human T cell clones were shown to recognize one or more of the mycobacterial stress proteins.

Stress Proteins are Immune Targets in Infections by Pathogens

The observation that stress proteins are important targets of the immune response to mycobacterial infection and the knowledge that the major stress proteins are conserved and abundant in other organisms suggested that stress proteins are likely to be immune targets in many infections by pathogens. Indeed, that is now clearly the case. Antigens from a wide variety of infectious agents have been identified as members of stress protein families. The major stress protein antigen recognized by antibodies in bacterial infections is hsp60. "Common antigen", an immunodominant protein antigen long known to be shared by most bacterial species, turns out to be hsp60. Shinnick, T. M., et al., *Infect. Immun.*, 56:446 (1988); Thole, J. E. R., et al., *Microbial Pathogenesis*, 4:71-83 (1988). Stress proteins have also been identified as immune targets in most major human parasite infections. Bianco, A. E., et al., *Proc. Natl. Acad. Sci. USA*, 83:8713 (1986); Nene, V., et al., *Mol. Biochem. Parasitol.*, 21:179 (1986); Ardeshir, F., et al., *EMBO J*, 6:493 (1987); Hedstrom, R., et al., *J. Exp. Med*, 165:1430 (1987); Selkirk, M. E., et al., *J. Cell Biochem.*, 12D:290 (1988), Engman, D. M., et al., *J. Cell Biochem.*, 12D: Supplement, 290 (1988); Smith, D. F., et al., *J. Cell Biochem.*, 12D:296 (1988). Antibodies to hsp70 have been identified in the sera of patients suffering from malaria, trypanosomiasis, leishmaniasis, schistosomiasis and filariasis. Hsp90 is also a target of antibodies in trypanosomiasis and a member of the small hsp family is recognized in some patients with schistosomiasis.

Proteins homologous to stress proteins have also been identified in viruses. Recently, a protein encoded by the RNA genome of the Beet Yellows Closterovirus, a plant virus, has been shown to be homologous to hsp70. Agranovsky, A. A., et al., *J. Mol. Biol.*, 217: 603-610 (1991). In addition, stress protein induction occurs in eukaryotic cells following infection by diverse viruses in vitro. Collins, P. L., and Hightower, L. E., *J. Virol.*, 44:703-707 (1982); Nevins, J. R., *Cell*, 29:913-939 (1982); Garry, R. F. et al., *Virology*, 129:391-332 (1988); Khandjian, E. W. and Turler, H., *Mol. Cell Biol.*, 3:1-8 (1983); LaThangue, N. B., et al., *EMBO J.*, 3:267-277 (1984); Jindal, S. and Young, R., *J. Viral*, 66:5357-5362 (1992). CTL that recognize these neo-antigens could limit the spread of virus by killing infected cells, possibly before substantial amounts of mature virus are assembled, and by secreting the lymphokine γ-interferon. Pestka, S., in: *Methods Enzymol.*, Interferons, Part A., Vol. 79 Academic Press, New York, pp. 667 (1981). Evidence consistent with this idea is emerging. Koga et al., (1989) have shown that infection of primary murine macrophages with CMV rendered them susceptible as targets for MHC-I restricted $CD8^+$ CTL specific for linear epitopes of *M. tuberculosis* hsp60. Koga, T., et al. (1989). Although the epitope recognized by these CTL on infected macrophages was not defined, it is tempting to speculate that a cross-reactivity with self hsp60 epitopes is being observed. Indeed, the same groups showed that a homologous hsp60 is constitutively present in macrophages and is upregulated by γ-interferon stimulation.

Stress Proteins as Immune Targets in Transformed Cells

Stress proteins appear to be produced at high levels in at least some transformed cells. Bensaude, O. and Morange, M., *EMBO J.*, 2: 173-177 (1983). An 86 kDA murine tumor antigen has been found to be homologous to representatives of the hsp90 family in yeast and *Drosophila*. Ullrich, S. J., *Proc. Natl. Acad. Sci., USA*, 83: 3121-3125 (1986). Immunization of mice with the purified protein led to inhibition of tumor growth in 95% of experimental animals that had been seeded with cultured tumor cells. All of the protected mice had high titers of anti-hsp90 serum antibody which was able to precipitate murine hsp90 from lysates of heat shocked mouse embryo cells. Again, a role for autoreactive lymphocytes is implied, since T cells capable of recognizing autologous cells stressed by transformation could help eliminate nascent tumor cells.

Stress Proteins and Autoimmune Processes

Rheumatoid arthritis is characterized by a chronic proliferative and inflammatory reaction in synovial membranes which is thought to involve autoimmune processes. Rat adjuvant arthritis resembles human rheumatoid arthritis in many respects, and has been used as an experimental animal model for human disease. Pearson, C. M., *Arthritis Rheum.*, 7:80-86 (1964). Adjuvant arthritis can be induced in rats with a single intradermal injection of killed *M. tuberculosis* in complete Freund's adjuvant. An autoimmune process involving T lymphocytes appears to be responsible for the generation of the disease. Holoshitz, J., et al., *Science*, 219:56-58 (1983). T cell lines isolated from the draining lymph nodes of arthritic rats and propagated in vitro by stimulation with *M. tuberculosis*-pulsed syngeneic antigen presenting cells can cause a transient form of the disease when transferred to irradiated rats. Since care was taken in these experiments to exclude the transfer of contaminating *M. tuberculosis*, this result strongly suggests that the clinical effects of the disease are a consequence of an autoimmune reaction in which the autoantigen is shared with *M. tuberculosis*.

The rat and *M. tuberculosis* antigens recognized by the arthritogenic T cells have been sought for a number of years. A number of different proteins present in synovial membranes have been proposed to be the cross-reactive rat antigen, but were later discounted as procedures for the purification of these proteins improved. van Eden, W., et al., *Proc. Natl. Acad. Sci., USA*, 82:5117-5120 (1985); Holoshitz, J., et al., *Science*, 219:56-58 (1983). The *M. tuberculosis* antigen recognized by the arthritogenic T cells was recently shown to be a 65 kDa protein (van Eden, W., et al., *Nature*, 331: 171 (1988), which has now been shown to be hsp60 (see the Example 1). Using a combination of truncated recombinant 65 kDa proteins and peptides, a nine amino acid epitope of hsp60 has been identified as the minimum stimulatory sequence for arthritogenic T cell clones in proliferation assays. Now that it is clear that some arthritogenic T cells recognize the mycobacterial hsp60, it is quite possible that the rat autoantigen is also hsp60.

The results obtained in the adjuvant arthritis model led investigators to determine whether T lymphocytes from human rheumatoid arthritis patients also recognize mycobacterial antigens. These investigators have found not only that patients with rheumatoid arthritis have T cells that recognize *M. tuberculosis* antigens, but that these T cells have diverse phenotypes. Substantial proliferative responses to mycobacterial extracts are observed with uncloned T cells (predominantly $CD4^+$) from both synovial infiltrates and peripheral blood, although responses are generally greater in synovial infiltrates. Abrahamson, T. G., et al., *Scand. J. Immunol.*, 7:81-90 (1978); Holoshitz, J., et al., *Lancet ii*, 305-306 (1986). Holoshitz et al. found that 4 of 5 T cell clones isolated from human rheumatoid synovia which respond to *M. tuberculosis* antigens were $CD4^-$ $CD8^-$ cells with γ/δ T cell receptors. Holoshitz, J., et al., *Nature*, 339:226-229 (1989). This observation is interesting because γ/δ T cells have yet to be assigned a role in immunity. One of the γ/δ clones was tested for its ability to respond to purified mycobacterial hsp60 and was found to be positive in proliferation assays. Due to the conserved nature of stress proteins, these T cells have the potential for autoreactivity. Lamb and coworkers have shown that polyclonal T cells from synovial infiltrates recognize both mycobacterial hsp60 and hsp70. Lamb, J. R., et al., *Intl. Immunol.*, in press (1989). The population of T cells that recognize the mycobacterial stress proteins were shown to respond to *E. coli* hsp60 and hsp70 and, most interestingly, human hsp70 purified from heat shocked macrophages. Thus, immune responses to conserved stress protein determinants, perhaps initiated by bacterial infection (not necessarily by mycobacteria), may play an important role in autoimmune pathology in rheumatoid arthritis, as well as in adjuvant arthritis.

Stress Proteins and Immune Surveillance

A variety of different T cell types has now been shown to recognize highly conserved stress protein determinants. The ability of cells to respond to stress by increasing the levels of the highly conserved stress proteins; the presence of T cells of diverse phenotypes in healthy individuals that are capable of recognizing self stress protein determinants; and observations that stress responses are induced by pathogenic infections and by cell transformation, all suggest a model of immune surveillance in which self-reactive T cells provide a first line of defense against infection and transformation by recognizing and helping to eliminate stressed autologous cells, as well as cells infected with intracellular pathogens. The pool of lymphocytes that recognize conserved stress protein determinants might be induced during establishment of natural microbial flora on the skin and in the gut, and maintained by frequent stimulation by pathogens, such as bacteria and viruses, as well as other stressful stimuli encountered during a normal lifetime. This model is attractive because it provides a way in which the immune system could exploit the existence of conserved epitopes in stress proteins to respond immediately to antigenically diverse pathogens and cellular changes, producing an initial defense that need not await the development of immunity to novel antigens.

The lymphocytes which recognize conserved stress protein determinants must be capable of discriminating between normal and stressed cells. Since many stress proteins are constitutively expressed in normal cells, although at lower levels than in stressed cells, the potential for autoreactivity is ever-present. Normal cells may escape destruction by expressing only substimulatory levels of stress protein determinants on their surfaces. In addition, stress proteins may only be processed and presented during stress, and it may be relevant that many stress proteins have altered intracellular locations during stress. Finally, immune regulatory networks may prevent activation of autoreactive T cells under normal conditions. The regulatory constraints required by this system might occasionally break down, perhaps during stress caused by bacterial or viral infections, leading to autoimmune disease. Rheumatoid arthritis may be such a disease.

Modulation of Immune Response

The precise relationship between stress proteins and the host immune response to infection is as yet undefined. When cells are subjected to a variety of stresses, they respond by selectively increasing the synthesis of a limited set of stress proteins. Some stress proteins, including the products of DnaK and GroEL, are major constituents of the cell under normal growth conditions and are induced to even higher levels during stress. Lindquist, S., *Annu. Rev. Biochem.* 55: 1151-1191 (1986); Neidhardt, F. C. and R. A. VanBogelen, *In Escherichia coli and Salmonella Typhimurium*, Cellular and Molecular Biology, (eds. Neidhardt, F. C., Ingraham, J. L. Low, K. B. Magasanik, B. Schaechter, M. and Umbarger, H. E.) Am. Soc. Microbiol., Washington, D.C., pp. 1134-1345 (1987). It has now been demonstrated that stress-related proteins are targets of the immune response. Young, D. et al., *Proc. Natl. Acad. Sci. USA,* 85:4267-4270 (1988). It is reasonable to expect that immunodominant antigens would be found among such abundant proteins, as has now been shown to be the case.

According to the method of the present invention, it is possible to modulate the immune response in an individual, such as a human, other mammal or other vertebrate, by altering the individual's response to stress proteins. In particular, it is possible to enhance or induce an individual's response to a pathogen (e.g., bacteria, virus, parasites, or other organism or agent, such as toxins, toxoids) or to cancer cells or enhance or induce an upregulation of an individual's immune status (such as in an immune compromised individual or HIV-infected individual); and to decrease an individual's autoimmune response, such as occurs in some forms of arthritis. In addition, administration of a stress protein using the method of the present invention provides protection against subsequent infection by a pathogen. As demonstrated herein, stress proteins contain regions of highly conserved amino acid sequences and have been shown to be major immunodominant antigens in bacterial and other infections. Therefore, it is reasonable to expect stress proteins can be used to elicit strong immune responses against a variety of pathogens. The stress protein administered to induce or enhance an immune response to pathogens can be the stress protein of the pathogen against which an immune response is desired or other stress protein, a portion of that protein of sufficient size to stimulate the desired immune response or a protein or amino acid sequence which is the functional equivalent of the stress protein in that it is sufficiently homologous in amino acid sequence to that of the stress protein to be capable of eliciting the desired response (an immune response substantially similar to that which occurs in response to the stress protein) in the individual to whom it is administered. The term "sufficiently homologous in amino acid sequence to that of the stress protein" means that the amino acid sequence of the protein or polypeptide will generally show at least 40% identity with the stress protein amino acid sequence; in some cases, the amino acid sequence of a functional equivalent exhibits approximately 50% identity with the amino acid sequence of the stress protein.

Any stress-induced proteins or their functional equivalents can be used by the present invention to enhance or induce an immune response in an individual (e.g. a human, other mammal or vertebrate), against an infection by a pathogen, for immunotherapy against cancer cells, for generally upregulating an individual's immune status and for use in inducing immune tolerance in an individual or animal.

The stress proteins of the present invention can be administered in a variety of ways to modulate the immune response of an individual (e.g., a human, other mammal or other vertebrate). In one embodiment, the stress protein is administered as a vaccine which is comprised of the stress protein or a portion of the stress protein which is of sufficient size to stimulate the desired immune response. In this embodiment, the vaccine can be a "specific vaccine" which contains a specific stress protein of a particular pathogen against which an immune response is desired, such as a bacterial stress protein. In this case, since the pathogen's stress proteins are distinguishable from those of the host, it is possible to induce an immunoprophylactic response specific to the pathogen's stress proteins. Blander, S. J., et al., *J. Clin. Invest.,* 91:717-723 (1993). This can be carried out by administering a vaccine which includes all or a portion (e.g., sufficient amino acid sequence to have the desired stimulatory effect on immune response) of the pathogen's stress protein or of another protein having an amino acid sequence sufficiently similar to that of the stress protein sequence to stimulate the immune response to the pathogen's stress protein. Alternatively, in the case of a pathogen which does not contain stress proteins, (e.g. some viruses) or in the condition of neoplasia, stress proteins or highly conserved stress protein determinants, such as those shown to be recognized by a variety of T cells, can be administered as a type of "general" vaccine to achieve an upregulation of the immune response. Administration of such a vaccine will enhance the existing immune surveillance system. For instance, a vaccine which includes a bacterial, or other stress protein can be administered to enhance the immune system which will result in an immune response against a pathogen which does not contain stress proteins. Alternatively, this type of "general" vaccine can be used to enhance an individual's immune response against cancer or to generally upregulate an individual's immune status, such as in an immune compromised individual (e.g., an individual undergoing chemotherapy or an HIV-infected individual). In either case of this embodiment (specific or general vaccine), the immune response to the stress protein sequence will be increased and effects of the pathogen, disease condition or immune impairment will be reduced (decreased, prevented or eliminated).

In another embodiment, stress proteins can be used to enhance immune surveillance by applying local heat or any other substances or changes in condition which induce the stress response in the individual being treated. (This can also be employed in conjunction with the specific vaccine, described previously, administered to enhance an immune response to a stress protein-containing pathogen or in conjunction with the general vaccine, described above, administered to enhance the immune response against a pathogen which does not contain its own stress proteins, cancer, or to upregulate the immune status of an individual). For example, it is known that increased levels of stress proteins are produced in many types of cancer cells. Therefore, enhancement of the immune surveillance system, using this embodiment of the present invention as described, can be used to facilitate destruction and/or to prevent progression or establishment of cancer cells.

The method of the present invention can also be used to modify or modulate an individual's response to his or her own cells (e.g., as in autoimmune diseases). There are at least two ways in which the present invention can be used immunotherapeutically. First, stress proteins, such as heat shock proteins (e.g., hsp 70 and hsp60), are known to be involved in autoimmune disease. It is, thus, possible to turn down an individual's immune response, resulting in the individual becoming more tolerant of the protein. Second, because it is known that under some circumstances, one component of the immune response in certain autoimmune diseases can be to stress proteins, it is possible to selectively inhibit or interfere with the ability of immune cells which normally interact with such proteins to do so. This can be done, for example, by administering monoclonal antibodies that bind to specific T cell receptors and delete or disable such cells. Alternatively, rather than knocking out immune cells, the stress response in cells can be turned down by administering a drug capable of reducing a cell's ability to undergo the stress response. For example, a drug targeted to or specific for heat shock transcription factor, which is needed to stimulate heat shock genes, can be administered. The transcription factor is rendered nonfunctional or subfunctional and, as a result, cells' ability to undergo the stress response is also lessened.

In another embodiment of the present invention, the stress protein is administered as a vaccine which is comprised of two moieties: a stress protein and another substance (referred to as an antigen, e.g. protein, peptide, carbohydrate, lipid, organic molecule) against which an immune response is desired. The two moieties are conjugated or joined to form a single unit. Conjugation can be achieved by chemical means known to those skilled in the art (e.g. through a covalent bond between the stress protein and the second moiety; reductive amination) or, as demonstrated in Example 2, by recombinant techniques. If recombinant techniques are used to produce the conjugate, the result is a recombinant fusion protein which includes the stress protein and the antigen in a single molecule. This makes it possible to produce and purifiy a single recombinant molecule in the vaccine production process. In this embodiment, the stress protein can be seen to act as an adjuvant-free carrier, and it stimulates strong humoral and T cell responses to the substance to which the stress protein is fused. The stress protein can be conjugated to any substance against which an immune response is desired or to a portion of the substance sufficient to induce an immune response in an individual to whom it is administered. The substance includes but is not limited to proteins (e.g., ovalalbumin, Influenza virus Hemagglutinin, Human Immunodeficiency Virus p24), peptides (e.g., Human Immunodeficiency Virus peptides, melanoma antigen peptides), oligosaccharides (e.g., *Neiseria meningitidis* group B, *Streptococcus pneumoniae* type 14, *Hemophilis influenzae* type b), lipids, carbohydrates (e.g., glycolipid antigens in human cancers such as GD3, GM2, Gb3, Forssman antigen, Sialosyl-Le$^a$ antigen and glycoprotein antigens in human cancers such as CEA, AFP, PSA, Tn antigen), organic molecules or a combination thereof. Recent evidence demonstrating the effectiveness of such a vaccine indicates that mycobacterial hsp70 proteins when conjugated to other proteins act as adjuvant-free carriers. The humoral immune response to some peptides conjugated to mycobacterial hsp70 administered without any adjuvant was very similar to the antibody response to the same peptides administered in Freund's complete adjuvant. Lussow, A. R., et al., *Eur. J. Immun.*, 21:2297-2302 (1991). Barrios, C. et al., *Eur. J. Immun.*, 22:1365-1372 (1992).

The present invention also relates to compositions which are conjugates comprised a stress protein joined to another substance or component. For example, the present invention relates to a conjugate in which a stress protein is chemically linked to an antigen, or in which a stress protein is fused to an antigen (e.g., a fusion protein).

Figure 6:
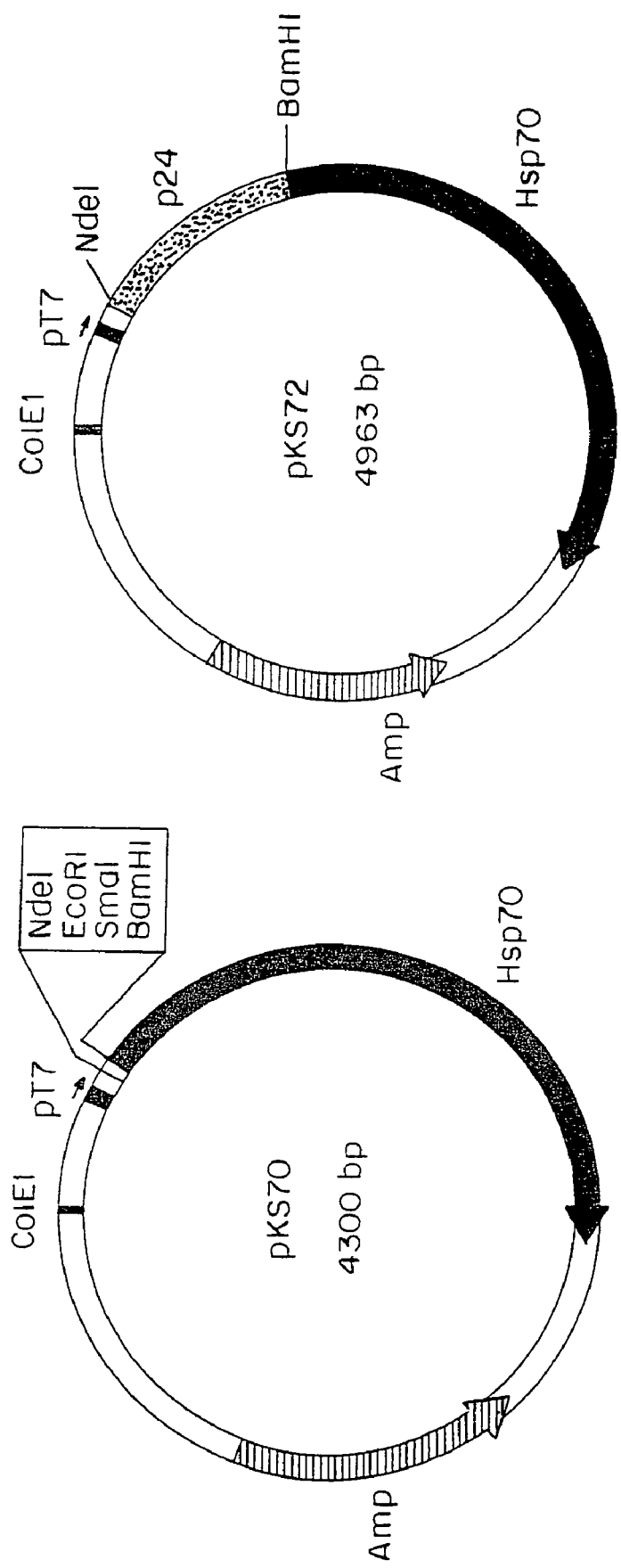
FIG. 6 is a schematic representation of the stress protein fusion vector, pKS70 containing the T7 RNA polymerase promoter, a polylinker and the mycobacterial tuberculosis hsp70 gene, and the stress protein fusion vector pKS72 containing the HIV p24 gag gene subcloned into the pKS70 vector.
Figure 7:
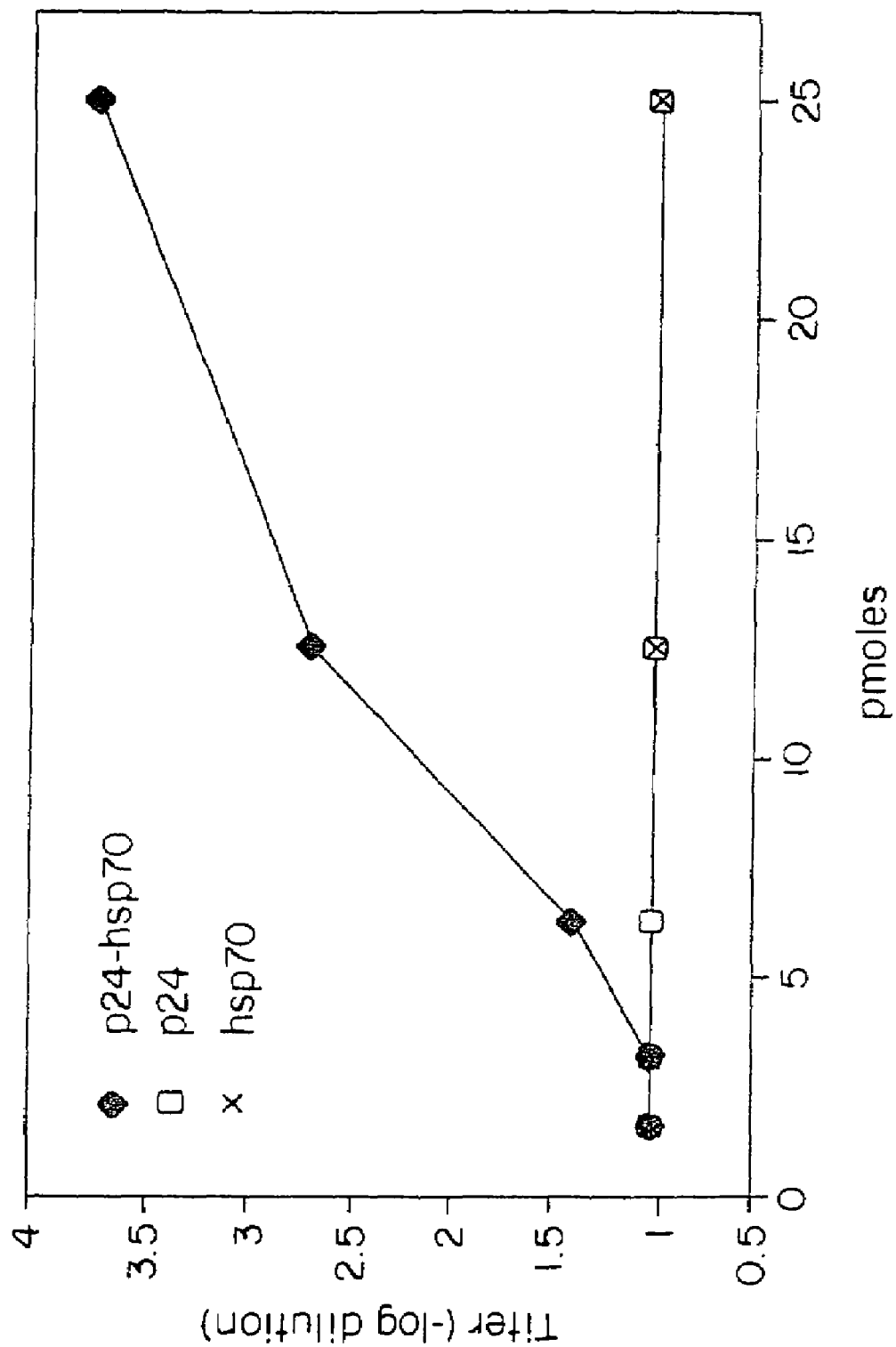
FIG. 7 is a graph illustrating the anti-p24 antibody titer in mice injected with the p24-hsp70 fusion protein, p24 alone and hsp70 alone.

As demonstrated in Example 3, the HIV p24 gag gene was subcloned into the stress protein fusion vector pKS70 (FIG. 6), containing the T7 RNA polymerase promoter, a polylinker and the mycobacterial tuberculosis hsp70 gene. The resulting vector pKS72 (FIG. 6) was used to produce the p24-hsp70 fusion protein in *E. coli*. Adjuvant-free, purified p24-hsp70 fusion protein was injected into Balb/c mice and as shown in FIG. 7, the anti-p24 antibody titer was 2.7 orders of magnitude higher in mice injected with the p24-hsp70 fusion protein than in mice injected with p24 alone or hsp70 alone. Mice injected with p24 and the adjuvant, alum, also produced an antibody response to p24. Finally, a demonstrable T cell response was seen in mice injected with the p24-hsp70 fusion protein and in mice injected with p24 alone.

In another embodiment of the present invention, the stress protein or a portion of the stress protein which is of sufficient size to stimulate an immune response or an equivalent, is administered as an adjuvant, with another substance (referred to as an antigen) against which an immune response is desired. The stress protein can be used as an adjuvant with any substance or antigen against which an immune response is desired or to a portion of the substance sufficient to induce an immune response in an individual to whom it is administered. The substance includes proteins, peptides, oligosaccharides, lipids, carbohydrates, organic molecules or a combination thereof. Via linkage to a stress protein, strong and specific B and T cell mediated immunity can be generated in a mammalian host (e.g., mice, rabbits, humans) to virtually any organic molecule. This is particularly useful 1) with substances (e.g., antigens) which alone are non-immunogenic; 2) when adjuvants cannot be used or do not work well in combination with a particular antigen; 3) when the availability of purified antigen is limited, particularly with fusion proteins where the antigen is made using recombinant DNA technology; 4) where other carrier molecules, such as KLH, BSA, OVA or thyrogloulin, which additionally require adjuvants, are not effective or desirable; 5) there is a genetic restriction in the immune response to the antigen; 6) there is a pre-existing immunosuppression or non-responsiveness to an antigen (e.g., pediatric vaccines where infants and children under 2 years of age do not generate protective immunity to carbohydrate antigens well); and 7) the type of immune response achieved by other carriers or adjuvants is undesirable or ineffectual (i.e., stress protein conjugates could be used to bias toward either B or T cell immunity via proper dose, route and inoculation regimen).

The present invention also relates to a method of generating monoclonal or polyclonal antibodies to a substance using a conjugate comprised of a stress protein joined to the substance. In this embodiment, an effective amount of the conjugate (i.e., an amount which results in an immune response in the host) is introduced into a mammalian host which results in production of antibodies to the substance in the host. The antibodies are removed from the host and purified using known techniques (e.g., chromatography), thereby resulting in production of polyclonal antibodies. Alternatively, the antibodies produced using the method of the present invention can be used to generate hybridoma cells which produce monoclonal antibodies using known techniques (Kohler, G., et al., *Nature*, 256:495(1975) Milstein et al., *Nature*, 266:550-552(1977); Koprowski et al., *Proc. Natl. Acad. Sci*, 74:2985-2988 (1977); Welsh, *Nature*, 266:495(1977); Maniatis, T. et al., *Molecular Cloning*, A Laboratory Manual, Cold Spring Harbor Lab., Cold Spring Harbor, N.Y. (1982)).

The stress protein, stress protein portion, stress protein functional equivalent and the substance to which the stress protein is fused or conjugated present in the vaccine can be produced or obtained using known techniques. For example, the stress protein or stress protein portion can be obtained (isolated) from a source in which it occurs in nature, can be produced by cloning and expressing a gene encoding the desired stress protein or stress protein portion or can be synthesized chemically or mechanically.

An effective dosage of the stress proteins of the present invention as vaccines or adjuvants, to elicit specific cellular and humoral immunity to stress proteins, or to substances conjugated to the stress proteins, such as proteins or oligosaccharides, is in the range of 0.1 to 1000 ug hsp per injection, depending on the individual to whom the stress protein is being administered. Lussow, A. R., et al., *Eur. J. Immun.*, 21:2297-2302 (1991). Barrios, C. et al., *Eur. J. Immun.*, 22:1365-1372 (1992). The appropriate dosage of the stress protein for each individual will be determined by taking into consideration, for example, the particular stress protein being administered, the type of individual to whom the stress protein is being administered, the age and size of the individual, the condition being treated or prevented and the severity of the condition. Those skilled in the art will be able to determine using no more than routine experimentation, the appropriate dosage to administer to an individual.

Various delivery systems can be used to administer an effective dose of the vaccine of the present invention. Methods of introduction include, for example, intradermal, intramuscular, intraperitoneal, intravenous, subcutaneous, intranasal, epidural and oral routes. Any other convenient route of administration can be used (infusion of a bolus injection, infusion of multiple injections over time, absorption through epithelial or mucocutaneous linings such as, oral mucosa, rectal and intestinal mucosa) or a series of injections over time.

The present invention is further illustrated by the following exemplification, which is not intended to be limiting in any way.

EXEMPLIFICATION

Example 1

Isolation and Characterization of Mycobacterial Stress Protein Antigens

Recombinant DNA Clones.

The isolation and characterization of *M. tuberculosis* and *M. leprae* λgt11 genomic DNA clones with murine monoclonal antibodies have been described. Husson, R. N. and Young, R. A., *Proc. Natl. Acad. Sci., USA* 84:1679-1683 (1987); Young, R. A., et al., *Nature* (London) 316: 450-452 (1985). DNA was isolated from these clones and was manipulated by standard procedures. Davis, R. W., *Advanced Bacterial Genetics*: A Manual for Genetic Engineering (Cold Spring Harbor Lab., Cold Spring Harbor, N.Y.), (1980).

DNA Sequence Analysis.

DNA was subcloned into vector M13mp18 or M13mp19 (New England Biolabs), as suggested by the supplier. Dideoxynucleotide chain-termination reactions and gel electrophoresis of the sequenced produced were as described. Davis, R. W., *Advanced Bacterial Genetics*: A Manual for Genetic Engineering (Cold Spring Harbor Lab., Cold Spring Harbor, N.Y.), (1980). DNA sequences were determined for both strands of DNA. Computer analysis of sequences with UWGCG programs was as described by Devereux, J., et al., *Nucleic Acids Res.*, 12: 387-395 (1984).

Immunoblot Analysis.

*Escherichia coli* strain TG1 was transformed with the following plasmids by standard procedures (Maniatis, T., et al., *Molecular Cloning*, A Laboratory Manual (Cold Spring Harbor Lab., Cold Spring Harbor, N.Y.) (1982), with selection for ampicillin resistance: pND5, a derivative of pBR325 containing the *E. coli* GroEL genes (Jenkins, A. J., et al., *Mol. Gen. Genet.*, 202: 446-454 (1986); pUC8 (Vic, J., *Gene*, 19: 259-268 (1982); pUC8 with insert DNA for λgt11 clone Y3178 (*M. leprae* 65-kDa antigen, Young, R. A., et al., *Nature*, (London) 316: 450-452 (1985)) ligated in the EcoRI site.

Overnight cultures of *E. coli* strains in Luria-Bertani (LB) medium were centrifuged and resuspended in isotonic phosphate-buffered saline at a cell density corresponding to an absorbance of 2 at 600 nm. An equal volume of sample buffer containing 2% (wt/vol) $NaDodSo_4$ was added, and, after heating on a boiling water bath for 2 min, samples were electrophoresed on 12% (wt/vol) polyacrylamide gels in the presence of $NaDodSO_4$. Blots were prepared by electrophoretic transfer of the proteins to a nitrocellulose membrane, and binding of monoclonal antibodies was assayed with a peroxidase-conjugated secondary antibody as described. Young, D. B., et al., *Infect. Immun.*, 55: 1421-1425 (1987).

Six *M. tuberculosis* and six *M. leprae* proteins have been implicated in the immune response to the mycobacterial pathogens (Table 1). To obtain clues to the normal cellular function of several of these mycobacterial antigens, DNA clones encoding these proteins, isolated by using monoclonal antibodies to probe lambda gt11 libraries (Husson, R. N. and Young, R. A., *Proc. Natl. Acad. Sci., USA*, 84: 1679-1683 (1987); Young, R. A., et al., *Nature*, (London) 316: 450-452 (1985)) were subjected to sequence analysis. The sequences elucidated have been submitted to the GenBank sequence database.

The Mycobacterial 71-k Da Antigen.

The 71-k Da antigen of *M. tuberculosis* is recognized by human T cells during infection (Table 1).

TABLE 1

MYCOBACTERIAL PROTEIN ANTIGENS

| Protein, kDA | Recognized by Human T Cells | Subjected to sequence analysis | Homology with known proteins |
|---|---|---|---|
| *M. tuberculosis* | | | |
| 71 | + | + | DnaK |
| 65* | + | + | GroEL |
| 38 | + | − | — |
| 19 | + | + | None |
| 14 | + | − | — |

TABLE 1-continued

MYCOBACTERIAL PROTEIN ANTIGENS

| Protein, kDA | Recognized by Human T Cells | Subjected to sequence analysis | Homology with known proteins |
|---|---|---|---|
| 12 | ND | – | — |
| *M. leprae* | | | |
| 70 | ND | – | DnaK |
| 65 | + | + | GroEL |
| 36 | + | – | — |
| 28 | + | – | — |
| 18 | + | + | Plant Hsp |
| 12 | ND | – | — |

Mycobacterial protein antigens, their recognition by human T cells, and homology of the deduced mycobacterial protein sequences to known proteins are summarized.
ND, not determined;
+, yes;
–, no
*Includes data derived from study of the 65-kDA antigens of *M. bovis* BCG (*Bacillus* Calmette-Gurein), which is identical to the *M. tuberculosis* 65-kDA antigen.
+ A. S. Mustafa, J. R. Lamb, D. Young and R. A. Young, unpublished data.

The insert DNA of lambdagt11 clone Y3271 (Husson, R. N., et al., *Proc. Natl. Acad. Sci, USA*, 84: 1679-1683 (1987), was sequenced to obtain amino acid sequence information for the 71-kDa antigen of *M. tuberculosis*. This clone produces a beta-galactosidase fusion protein containing the carboxyl-terminal one-third of the 71-kDa antigen exhibiting 40% amino acid sequence identity with the comparable segment of the dnaK gene product from *E. coli* (Bardwell, J. C., et al., *Proc. Natl. Sci., USA*, 81: 848-852 (1984)), (FIG. 1). FIG. 1A shows the extent of sequence similarity between portions of the mycobacterial and the *E. coli* 70-k Da polypeptides. Sequences transcriptionally downstream from the mycobacterial 71-k Da gene predict a 356-amino acid protein homologous to the *E. coli* dnaJ gene product (unpublished data), indicating that the *E. coli* dnaK-dnaJ operon structure is conserved in *M. tuberculosis* and consistent with the conclusion that the mycobacterial 71-kDa antigen is a homologue of the *E. coli* dnaK gene product. The product of the dnaK gene is a member of the 70-kDa heat shock protein family that is highly conserved among prokaryotes and eukaryotes (Bardwell, J. C., et al., *Proc. Natl. Acad. Sci., USA*, 81: 848-852 (1984); Lindquist, S., *Annu. Rev. Biochem.*, 55: 1151-1191 (1986).

The *M. leprae* 70-k Da antigen cross-reacts with monoclonal antibodies directed to the *M. tuberculosis* 70-kDa antigen. *M. tuberculosis* and *M. leprae* are both members of the 70-k Da heat shock protein family of stress proteins.

The Mycobacterial 65-kDa Antigen.

The 65-kDa antigens of *M. tuberculosis* and *M. leprae* are involved in the human T-cell response to mycobacterial infection (Table 1). Genes encoding these proteins have been isolated (Husson, R. N., and Young, R. A., *Proc. Natl. Acad. Sci., USA*, 84: 1679-1683 (1987); Young, R. A., et al., *Nature*, (London) 316: 450-452 (1985)) and sequenced (Shinnick, T. M., *J. Bacteriol.*, 169: 1080-1088 (1987); Mehram, V., et al., *Proc. Natl. Acad. Sci., USA* 83: 7013-7017 (1986)), revealing that the amino acid sequences of the 65-kDa antigens of *M. tuberculosis* (SEQ ID NO: 4) and *M. leprae* (SEQ ID NO: 3) are 95% identical. These proteins sequences exhibited no significant sequence similarity to proteins in the GenBank database.

Figure 1B:
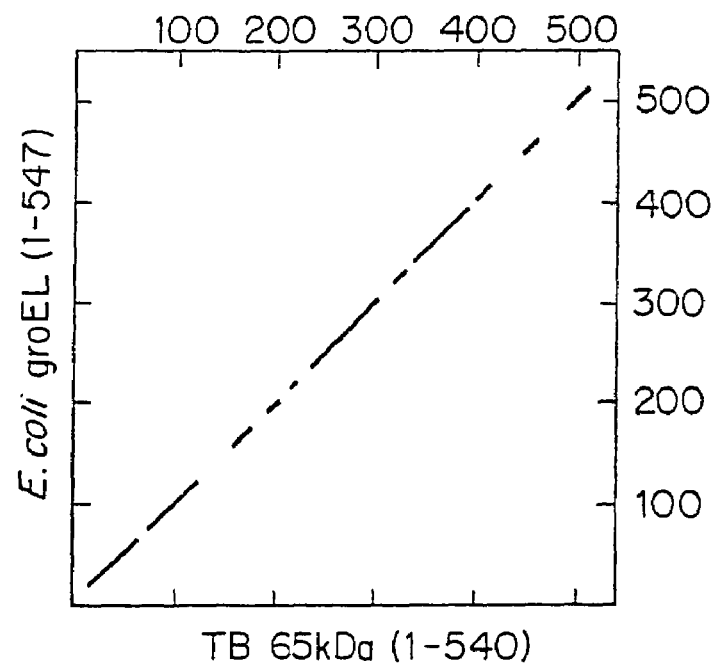
FIG. 1B is a graph illustrating the sequence similarity between portions of the *M. tuberculosis* 65-kDa antigen (residues 1-540; TB 65 kDa) and the *E. coli* GroEL protein (residues 1-547).

Identification of these proteins was based on the observation that some monoclonal antibodies directed against the mycobacterial 65-kDa antigens cross-react with an *E. coli* protein of 60 kDa. *E. coli* cells transformed with the plasmid pND5 (Sanger, F., et al., *Proc. Natl. Acad. Sci., USA* 74: 5463-5467 (1977), which contains the *E. coli* gro E genes, had been shown to accumulate large amounts of the 60-kDa protein. A comparison of the mycobacterial 65-kDa protein sequences with those determined for *E. coli* groEl (C. Woolford, K. Tilly, C. Georgopoulous, and R. H., unpublished data) revealed the extent of the sequence similarity as shown in FIG. 1B.

The 60-kDa Gro EL protein is a major stress protein in *E. coli*. Lindquist, S., *Annual. Rev. Biochem.*, 55: 1151-1191 (1986); *Nature*, 333: 330-334 (1988). There is some evidence that the mycobacterial 65-kDa proteins accumulate in response to stress: *Mycobacterium bovis* BCG (*bacillus* Calmette-Guerin) cultures grown in zinc-deficient medium are substantially enriched in this protein (De Bruyn, J., et al., *Infect. Immun.* 55: 245-252 (1987)). This infers that the 65-kDa proteins of *M. tuberculosis* and *M. leprae* are homologues of the *E. coli* Gro EL protein.

Other Mycobacterial Antigens.

T lymphocytes that respond to the *M. tuberculosis* 19-kDa antigen and the *M. leprae* 18-kDa antigen have been observed in humans with tuberculosis and leprosy, respectively (Table 1). DNA encoding these antigens was sequenced from the λgt11 clones Y3148 (Husson, R. N. and Young, R. A., *Proc. Natl. Acad. Sci., USA* 84: 1679-1683 (1987); and Y3179 (Young, R. A., et al., *Nature*, (London) 316: 450-452 (1985)), respectively. The *M. tuberculosis* 19-kDa protein sequence predicted from the DNA exhibited no significant sequence similarity to proteins in the GenBank database.

However, the *M. leprae* 18-kDa protein sequence was similar to the soybean 17-kDa protein heat shock protein, a protein representation of a major class of plant heat shock proteins (Schoffl, F. and Van Bogelen, R. A., *In: Escherichia coli and Salmonella typhimurium*, Cellular and Molecular Biology, Am. Soc. Microbiol., Washington, D.C. (1987).

Example 2

Construction of Stress Protein-Fusion Vaccines for Use as Adjuvant-Free Carriers in Immunizations Recombinant Fusion Vectors.

Figure 5:
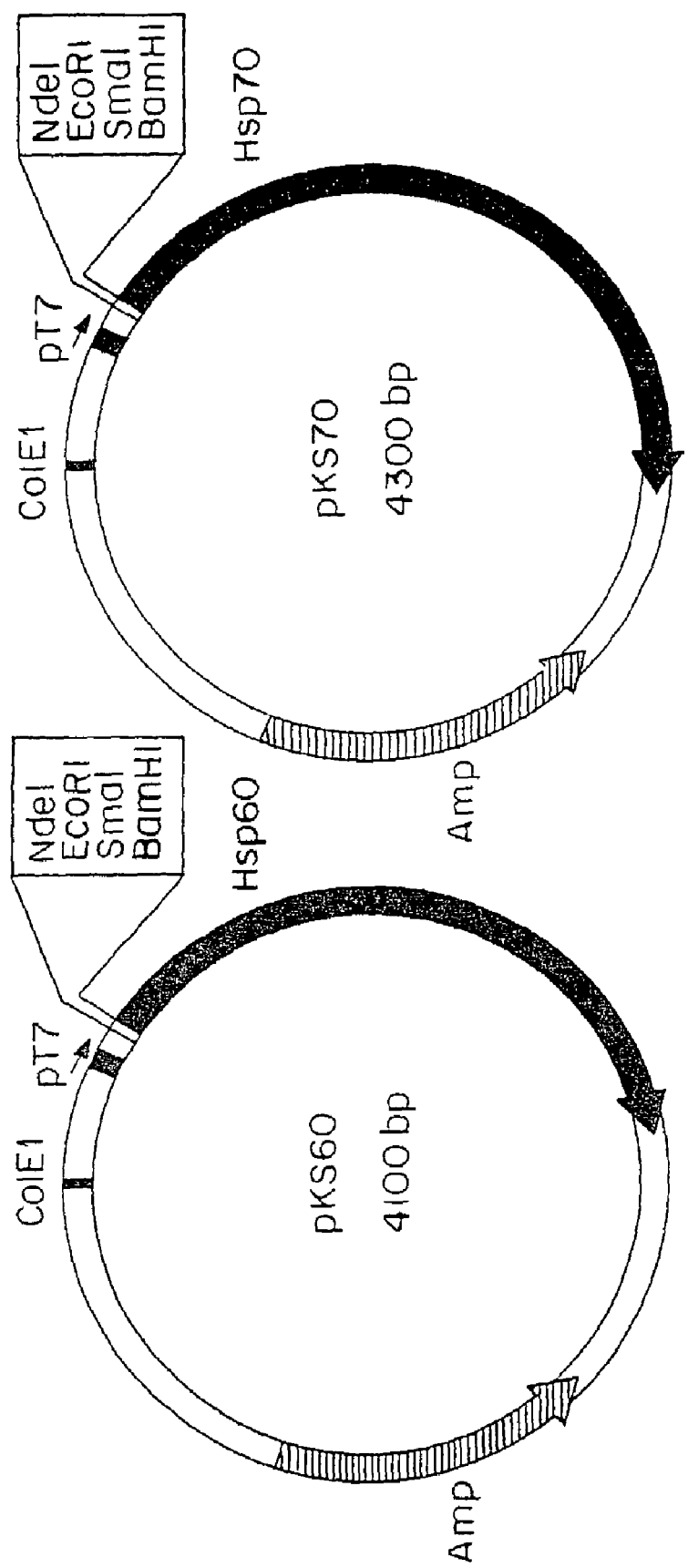
FIG. 5 is a schematic representation of selected stress protein fusion vectors which contain a polylinker with multiple cloning sites permitting incorporation of a gene of interest.

A series of stress protein fusion vectors for use in *E. coli* were constructed and are shown in FIG. 5. These vectors contain the T7 RNA polymerase promoter fused to the *M. bovis* BCG hsp70 gene or the *M. bovis* BCG hsp60 gene. The vectors also contain a polylinker with multiple cloning sites, permitting incorporation of a gene of interest so that the antigen encoded by that gene is expressed as a fusion protein with the stress protein. A subset of these vectors permit incorporation of the foreign gene with a coding sequence for a C-terminal 6-Histidine "tag" for ease of fusion protein purification. Thus far, recombinant clones have been generated that produce hsp70 proteins fused to HIV gag and HIV pol proteins.

Purification of Stress Protein Fusions.

Two strategies have been developed to purify the recombinant fusion proteins. The T7 system usually produces such large amounts of protein that it forms inclusion bodies, permitting purification by centrifugation. The preliminary results indicate that an hsp70-HIV gag fusion protein accounts for about 20% of total *E. coli* protein in the T7 system. If necessary, other fusion proteins can be purified via the 6-Histidine "tag".

Example 3

Adjuvant-Free Carrier Effect of HSP70 In Vivo

The stress protein fusion vector pKS70 (FIG. 6), containing the T7 RNA polymerase promoter, a polylinker and the mycobacterial tuberculosis hsp70 gene, was constructed. The HIV p24 gag gene was subcloned into pKS70 using the Nde1 and BamHI sites and the resulting pKS72 vector (FIG. 6) was used to produce the p24-hsp70 fusion protein in E. coli. The fusion protein was purified as inclusion bodies and further purified using ATP-agarose chromatography and MonoQ ion exchange chromatography.

The p24-hsp70 protein in phosphate buffered saline (PBS), in the absence of an adjuvant, was injected intraperitoneally into Balb/c mice. As controls, the p24 protein alone in PBS or the hsp70 protein alone in PBS was injected into different groups of mice. Three weeks later, the mice were boosted and finally, three weeks after the boost, the mice were bled. The anti-p24 antibody titer was then determined by ELISA. Mice injected with 25 pmoles of p24-hsp70 had antibody levels 2.7 orders of magnitude higher than mice injected with p24 alone or hsp70 alone (FIG. 7). Results of experiments in which mice were injected with p24 and the adjuvant, alum, also showed that there was an antibody response to p24. In addition, mice injected with the p24-hsp70 fusion protein and mice injected with p24 alone produced a demonstrable T cell response.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

---

What is claimed is:

1. A method for inducing or enhancing an immune response in an individual, the method comprising administering to the individual a composition comprising a stress protein joined via a peptide bond to a melanoma antigen peptide, wherein the composition, when administered to the individual, induces or enhances an immune response against the melanoma antigen.

2. The method of claim 1, wherein the stress protein is a heat shock protein (hsp).

3. The method of claim 1, wherein the stress protein is a mycobacterial stress protein.

4. The method of claim 1, wherein the stress protein is a member of the hsp70 family or the hsp60 family.

5. The method of claim 1, wherein the stress protein is a member of the groES family, the DnaJ family, the hsp90 family, or the small molecular weight family of stress proteins.

6. The method of claim 3, wherein the mycobacterial stress protein is an *M. bovis*, *M. leprae*, or *M. tuberculosis* stress protein.

7. The method of claim 6, wherein the mycobacterial stress protein is an *M. bovis* BCG hsp65 protein.

8. The method of claim 6, wherein the mycobacterial stress protein is *M. tuberculosis* hsp70.

9. The method of claim 1, wherein the composition is administered intramuscularly or intravenously.

10. The method of claim 1, wherein the individual is a human.

* * * * *